(12) United States Patent
Murakami

(10) Patent No.: US 7,815,658 B2
(45) Date of Patent: Oct. 19, 2010

(54) ULTRASONIC TREATMENT APPARATUS, METHOD OF ASSEMBLING AND DISASSEMBLING ULTRASONIC TREATMENT APPARATUS, AND ULTRASONIC TREATMENT SYSTEM

(75) Inventor: Eiji Murakami, Hachioji (JP)

(73) Assignee: Olympus Corporation (JP)

( * ) Notice: Subject to any disclaimer, the term of this patent is extended or adjusted under 35 U.S.C. 154(b) by 679 days.

(21) Appl. No.: 11/414,775

(22) Filed: Apr. 28, 2006

(65) Prior Publication Data

US 2006/0241532 A1    Oct. 26, 2006

Related U.S. Application Data

(63) Continuation of application No. PCT/JP2004/012569, filed on Aug. 31, 2004.

(30) Foreign Application Priority Data

Mar. 30, 2004   (JP) .............................. 2004-098226
Mar. 30, 2004   (JP) .............................. 2004-098227
Mar. 30, 2004   (JP) .............................. 2004-098228

(51) Int. Cl.
*A61B 17/32* (2006.01)
*A61B 17/00* (2006.01)

(52) U.S. Cl. .......................... 606/169; 606/205; 604/22

(58) Field of Classification Search ................... 433/86, 433/119; 600/437; 604/22; 606/169–174, 606/1, 41–52, 205–210

See application file for complete search history.

(56) References Cited

U.S. PATENT DOCUMENTS 4,887,612 A * 12/1989 Esser et al. .................. 600/564

(Continued)

FOREIGN PATENT DOCUMENTS

CN          2820104          9/2006

(Continued)

OTHER PUBLICATIONS

English translation of Notification of Transmittal of Preliminary Report on Patentability dated Nov. 29, 2006 for PCT/JP2004/012569.

(Continued)

*Primary Examiner*—Anhtuan T Nguyen
*Assistant Examiner*—Ashley Cronin
(74) *Attorney, Agent, or Firm*—Ostrolenk Faber LLP

(57) ABSTRACT

An ultrasonic treatment apparatus includes a vibrator-assembly which generates ultrasonic vibration, a probe which is detachably mounted to the vibrator-assembly, and has a treatment-portion which performs treatment of a biological tissue in a distal end portion, and a main-body-unit-assembly to which the vibrator-assembly and the probe are detachably mounted, and in which the biological tissue is treated with the treatment-portion when an operator operates the main-body-unit-assembly while the probe is amounted. The main-body-unit-assembly includes a treatment-assembly which has an action-portion in a distal end portion facing the treatment-portion of the probe, and a handle-assembly which is detachably mounted to a proximal end portion of the treatment-assembly, and which brings the action-portion into contact with the treatment-portion of the probe or separates the action-portion from the treatment-portion while the handle-assembly is mounted to the proximal end portion of the treatment-assembly.

12 Claims, 25 Drawing Sheets

U.S. PATENT DOCUMENTS

| | | | |
|---|---|---|---|
| 6,099,537 | A | 8/2000 | Sugai et al. |
| 6,129,735 | A * | 10/2000 | Okada et al. ............. 606/169 |
| 6,193,709 | B1 * | 2/2001 | Miyawaki et al. ............ 606/1 |
| 2002/0107538 | A1 * | 8/2002 | Shibata et al. ............. 606/169 |
| 2003/0135136 | A1 | 7/2003 | Murakami |
| 2003/0191390 | A1 | 10/2003 | Murakami |

FOREIGN PATENT DOCUMENTS

| | | |
|---|---|---|
| EP | 1 327 420 A1 | 7/2003 |
| JP | 09-38099 | 2/1997 |
| JP | 10-005236 | 1/1998 |
| JP | 11-113918 | 4/1999 |
| JP | 2002-224132 | 8/2002 |
| JP | 2002-224133 | 8/2002 |
| JP | 2003-265496 | 9/2003 |
| JP | 2005-278932 | 10/2005 |
| JP | 2005-278933 | 10/2005 |
| JP | 2005-278934 | 10/2005 |

OTHER PUBLICATIONS

International Search Report PCT/JP2004/012569 dated Nov. 19, 2004.

Office Action issued by the Chinese Patent Office on Dec. 8, 2006 for the corresponding Chinese Patent Application No. 200510062650X.

Translation of the Office Action issued by the Chinese Patent Office on Dec. 8, 2006 for the corresponding Chinese Patent Application No. 200510062650X.

Letter from German associate dated Jun. 30, 2009 forwarding the Search Report dated Jun. 29, 2009 to Japanese associate, including discussion of relevancy thereof.

Search Report issued by European Patent Office in connection with corresponding application No. EP 04 77 2525 on Jun. 29, 2009.

Office Action issued by the Japanese Patent Office on Nov. 24, 2009 in connection with corresponding Japanese Patent Application No. 2004-098227.

Translation of Office Action issued by the Japanese Patent Office on Nov. 24, 2009 in connection with corresponding Japanese Patent Application No. 2004-098227.

Office Action issued by the Japanese Patent Office on Nov. 24, 2009 in connection with corresponding Japanese Patent Application No. 2004-098228.

Translation of Office Action issued by the Japanese Patent Office on Nov. 24, 2009 in connection with corresponding Japanese Patent Application No. 2004-098228.

* cited by examiner

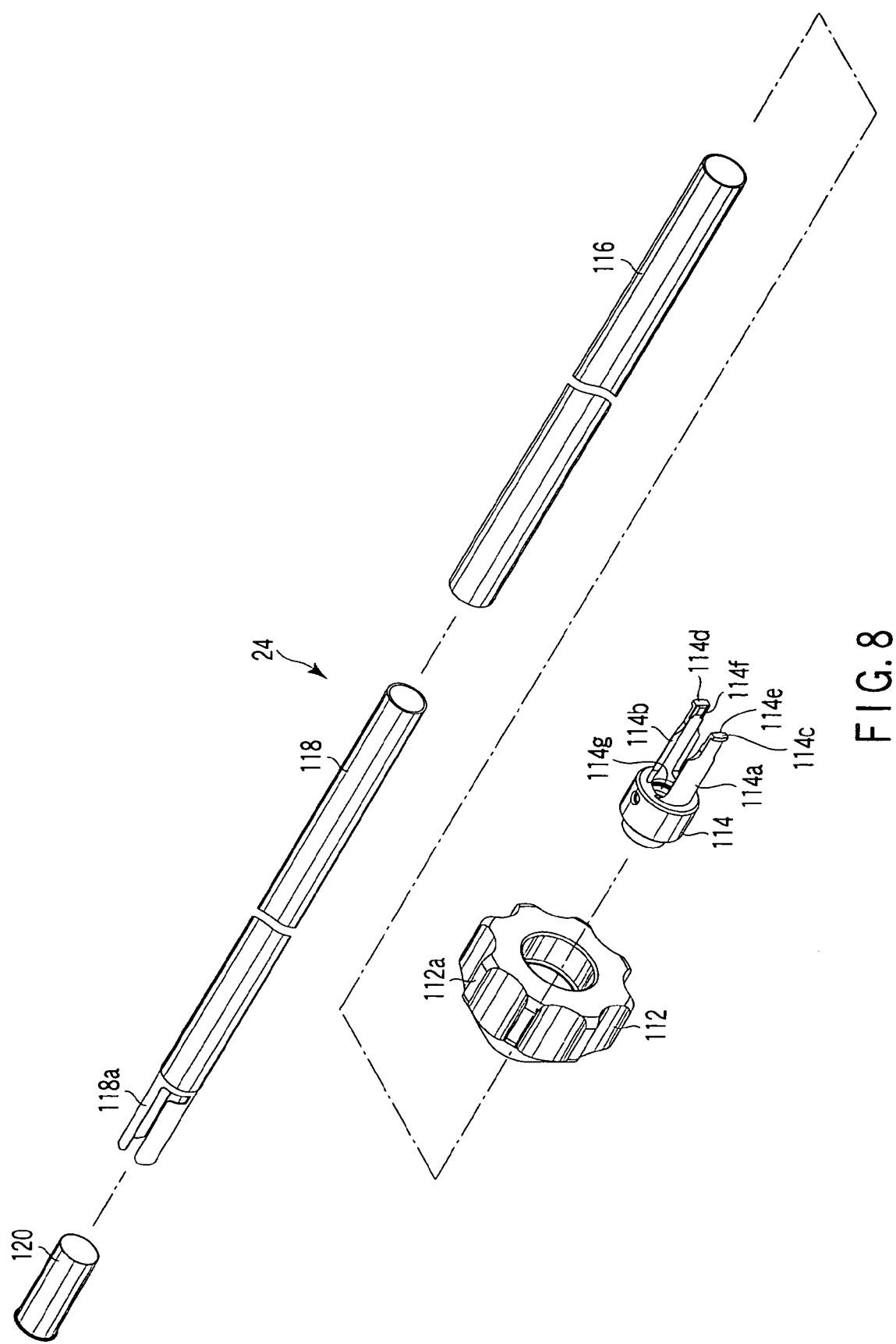

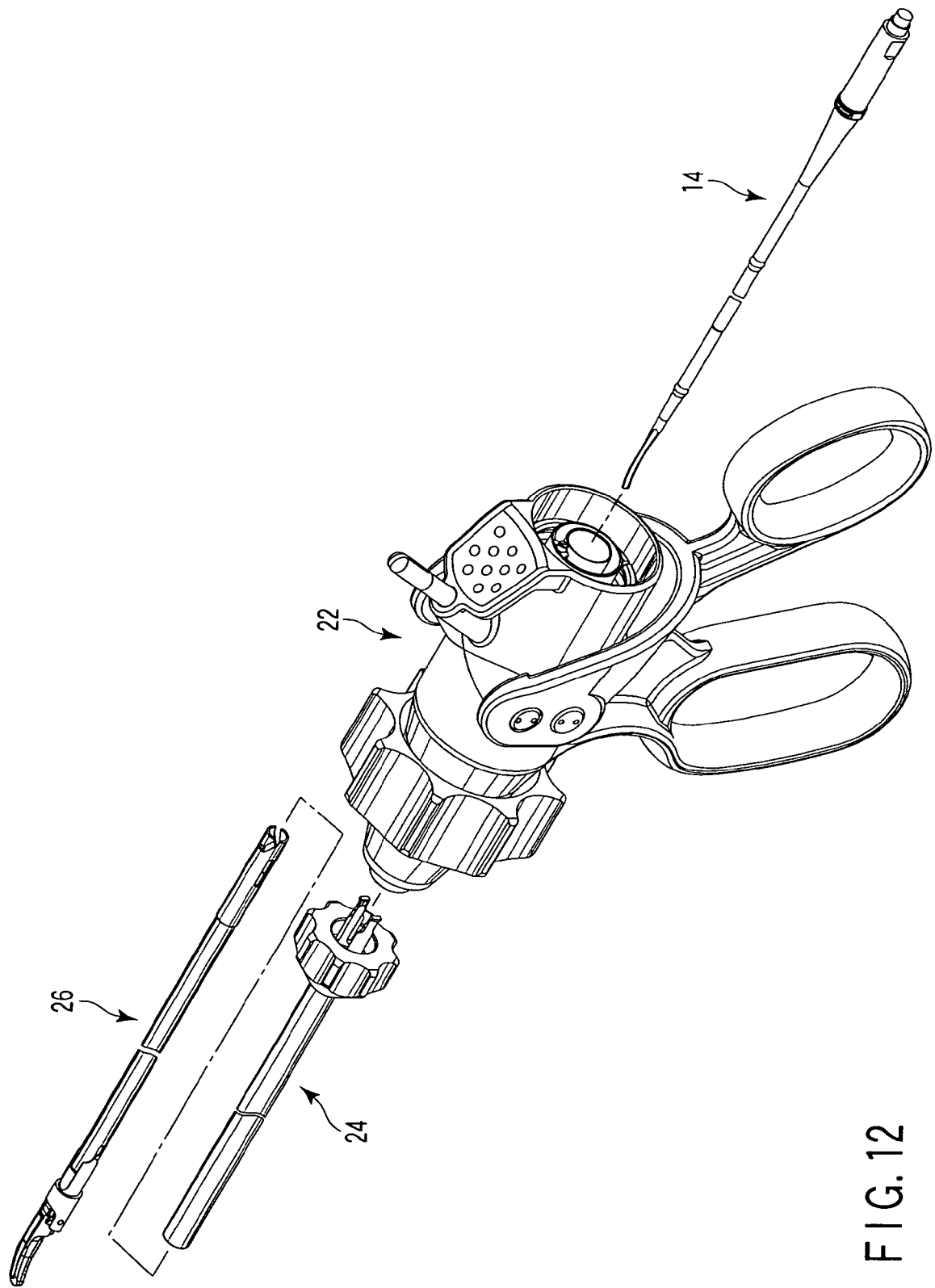
F I G. 12

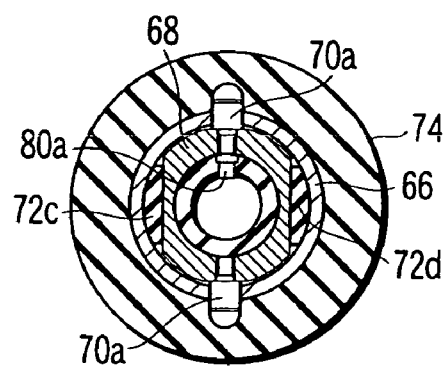
F I G. 18B

ULTRASONIC TREATMENT APPARATUS, METHOD OF ASSEMBLING AND DISASSEMBLING ULTRASONIC TREATMENT APPARATUS, AND ULTRASONIC TREATMENT SYSTEM

CROSS-REFERENCE TO RELATED APPLICATIONS

This is a Continuation Application of PCT Application No. PCT/JP2004/012569, filed Apr. 30, 2006, which was published under PCT Article 21(2) in Japanese.

This application is based upon and claims the benefit of priority from prior Japanese Patent Applications No. 2004-098226, filed Mar. 30, 2004; No. 2004-098227, filed Mar. 30, 2004; and No. 2004-098228, filed Mar. 30, 2004, the entire contents of all of which are incorporated herein by reference.

BACKGROUND OF THE INVENTION

1. Field of the Invention

The present invention relates to an ultrasonic treatment apparatus which can treat a biological tissue by utilizing ultrasonic vibration transmitted to an ultrasonic probe, a method of assembling the ultrasonic treatment apparatus, and an ultrasonic treatment system.

2. Description of the Related Art

For example, Jpn. Pat. Appln. KOKAI Publication No. 2002-224133 discloses an ultrasonic treatment instrument in which the treatment such as solidifying or cutting is performed on the biological tissue by the ultrasonic vibration while the biological tissue is gripped. The ultrasonic treatment instrument mainly includes a main body unit, a probe, and a vibrator unit. The main body unit, the probe, and the vibrator unit can be disassembled so as to be easily cleaned and repeatedly used.

In this kind of ultrasonic treatment instrument, the main body unit includes a long insertion portion which is inserted into a body cavity to perform the treatment, and an operation portion which is provided in a proximal end portion of the insertion portion. A distal end treatment portion which grips the biological tissue is provided in a distal end portion of the insertion portion. The distal end treatment portion includes a jaw and the treatment portion of the probe. The jaw is rotatably attached to the distal end portion of the insertion portion by a pin while facing the treatment portion of the probe. Therefore, the jaw can be opened and closed at the distal end portion of the insertion portion with respect to the treatment portion of the probe.

Generally, in the jaw, in order to prevent friction by the ultrasonic vibration of the probe, a grip member made of a resin material such as PTFE having a low friction coefficient is attached to a region which comes into contact with the treatment portion of the probe. An operation handle which operates opening and closing of the jaw is rotatably attached to the operation portion. The operation handle and the jaw are coupled to each other by a drive shaft passing through a channel in the insertion portion. The drive shaft proceeds and retreats in an axial direction of the insertion portion by operating the operation handle, and the jaw is opened and closed by transmitting drive force to the jaw.

A vibrator unit, into which a device for converting high-frequency current into the ultrasonic vibration is incorporated, is detachably attached onto a proximal end side of the operation portion. The probe which transmits the ultrasonic vibration is detachably connected to the vibrator unit by a screw or the like. The probe is inserted into a channel different from the drive shaft located in the operation portion and insertion portion of the main body unit. In the state in which the probe is assembled to the main body unit, the treatment portion located at the distal end of the probe faces the jaw while protruded past the distal end of the insertion portion.

In the ultrasonic treatment instrument, the grip member of the jaw is worn because the grip member is repeatedly used. The life of the ultrasonic treatment instrument is ended at the time when the grip member is completely worn. At this point, the cost is held down by replacing the main body unit with a new one when compared with the case where the whole of the ultrasonic treatment instrument is replaced. In cleaning the ultrasonic treatment instrument after use, the ultrasonic treatment instrument is cleaned using a dedicated cleaning adaptor which flushes the channel of the drive shaft, where a brush cannot be inserted, with a cleaning solution.

BRIEF SUMMARY OF THE INVENTION

An aspect of the invention provides an ultrasonic treatment apparatus includes a vibrator assembly which generates ultrasonic vibration; a probe which is detachably mounted to the vibrator assembly, and has a treatment portion which performs treatment of a biological tissue in a distal end portion; and a main body unit assembly to which the vibrator assembly and the probe are detachably mounted, and in which the biological tissue is treated with the treatment portion when an operator operates the main body unit assembly while the probe is amounted. The main body unit assembly includes a treatment assembly which has an action portion in a distal end portion facing the treatment portion of the probe; and a handle assembly which is detachably mounted to a proximal end portion of the treatment assembly, and which brings the action portion into contact with the treatment portion of the probe or separates the action portion from the treatment portion while the handle assembly is mounted to the proximal end portion of the treatment assembly.

BRIEF DESCRIPTION OF THE SEVERAL VIEWS OF THE DRAWING

FIG. 6A shows a transverse sectional view of the handle assembly of the main body unit assembly in the ultrasonic treatment instrument according to the first embodiment.

FIG. 6B shows a transverse sectional view of the handle assembly of the main body unit assembly in the ultrasonic treatment instrument according to the first embodiment.

FIG. 7A shows a transverse sectional view of the handle assembly of the main body unit assembly in the ultrasonic treatment instrument according to the first embodiment.

FIG. 7B shows a transverse sectional view of the handle assembly of the main body unit assembly in the ultrasonic treatment instrument according to the first embodiment.

FIG. 7C shows a transverse sectional view of the handle assembly of the main body unit assembly in the ultrasonic treatment instrument according to the first embodiment.

FIG. 8 is an exploded perspective view of the sheath assembly of the main body unit assembly in the ultrasonic treatment instrument according to the first embodiment.

FIG. 12 is a schematic perspective view showing a state in which the sheath assembly, the jaw assembly, and the probe are attached to and detached from a handle main body of the ultrasonic treatment instrument according to the first embodiment.

FIG. 13A is a schematic perspective view showing a state in which the jaw assembly is moved in an arrow α direction with respect to the sheath assembly to assemble the jaw assembly and the sheath assembly.

FIG. 13B is a schematic perspective view showing a state in which the jaw assembly is rotated in an arrow β direction with respect to the sheath assembly to assemble the jaw assembly and the sheath assembly.

FIG. 13C is a schematic perspective view showing a state in which the jaw assembly is assembled to the sheath assembly.

FIG. 14A is a schematic perspective view showing a state in which an insertion portion unit assembly, in which the sheath assembly and the jaw assembly are integrated, is moved in an arrow γ direction with respect to the main body unit assembly to assemble the insertion portion unit assembly and the handle assembly.

FIG. 14B is a schematic perspective view showing a state in which the insertion portion unit assembly is rotated in an arrow δ direction with respect to the handle assembly to assemble the insertion portion unit assembly and the handle assembly.

FIG. 14C is a schematic perspective view showing the assembled main body unit assembly.

FIG. 15A is a schematic perspective view showing a state in which a rotating knob of the handle assembly is moved in an arrow ε direction to rotate the insertion portion unit assembly in an arrow ζ direction with respect to the handle assembly.

FIG. 15B is a schematic perspective view showing a state in which the insertion portion unit assembly is rotated in the arrow ζ direction in FIG. 15A with respect to the handle assembly.

FIG. 15C is a schematic perspective view showing a state in which the ultrasonic treatment instrument is disassembled by drawing the insertion portion unit assembly in an arrow η direction with respect to the handle assembly.

FIG. 18B is a sectional view taken along arrow line 18A-18A in FIG. 18A of the main body unit assembly in the ultrasonic treatment instrument according to the second embodiment.

DETAILED DESCRIPTION OF THE INVENTION

The best mode for carrying out the invention will be described below with reference to the drawings.

A first embodiment will be described with reference to FIGS. 1 to 15C.

Figure 1:
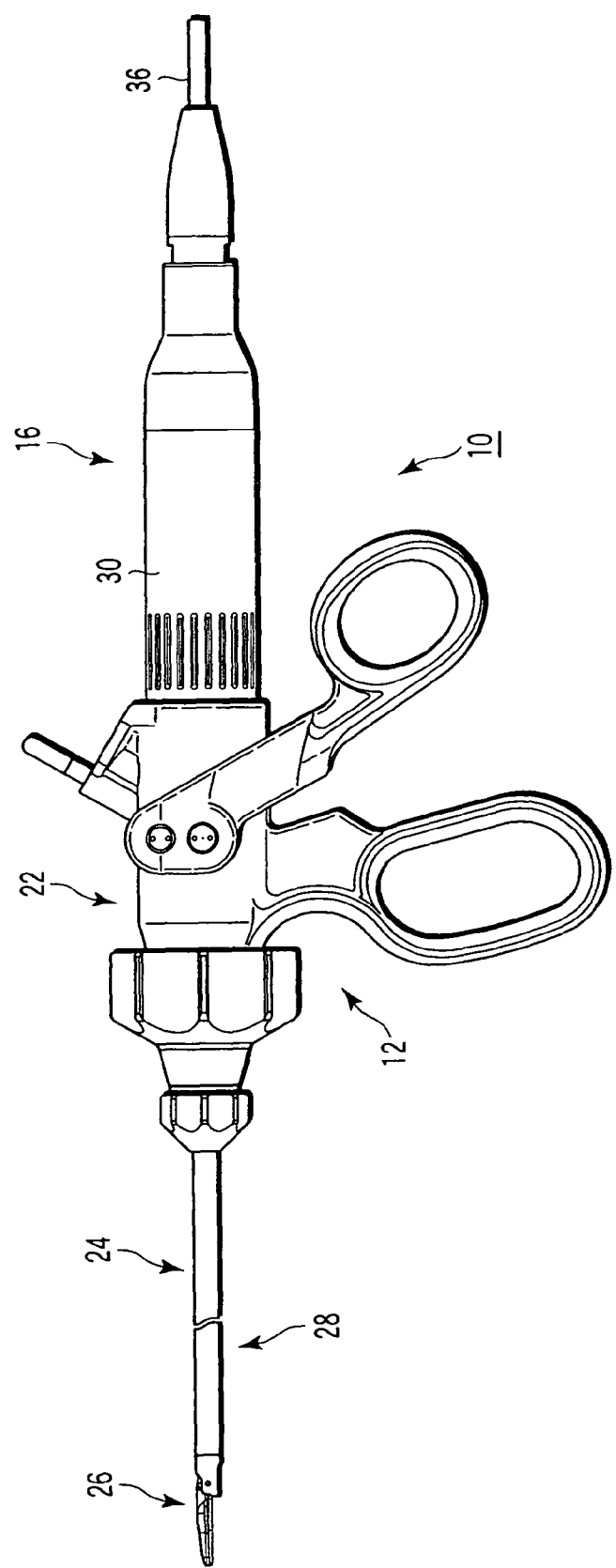
FIG. 1 is a schematic side view of an ultrasonic treatment instrument according to a first embodiment.
Figure 2A:
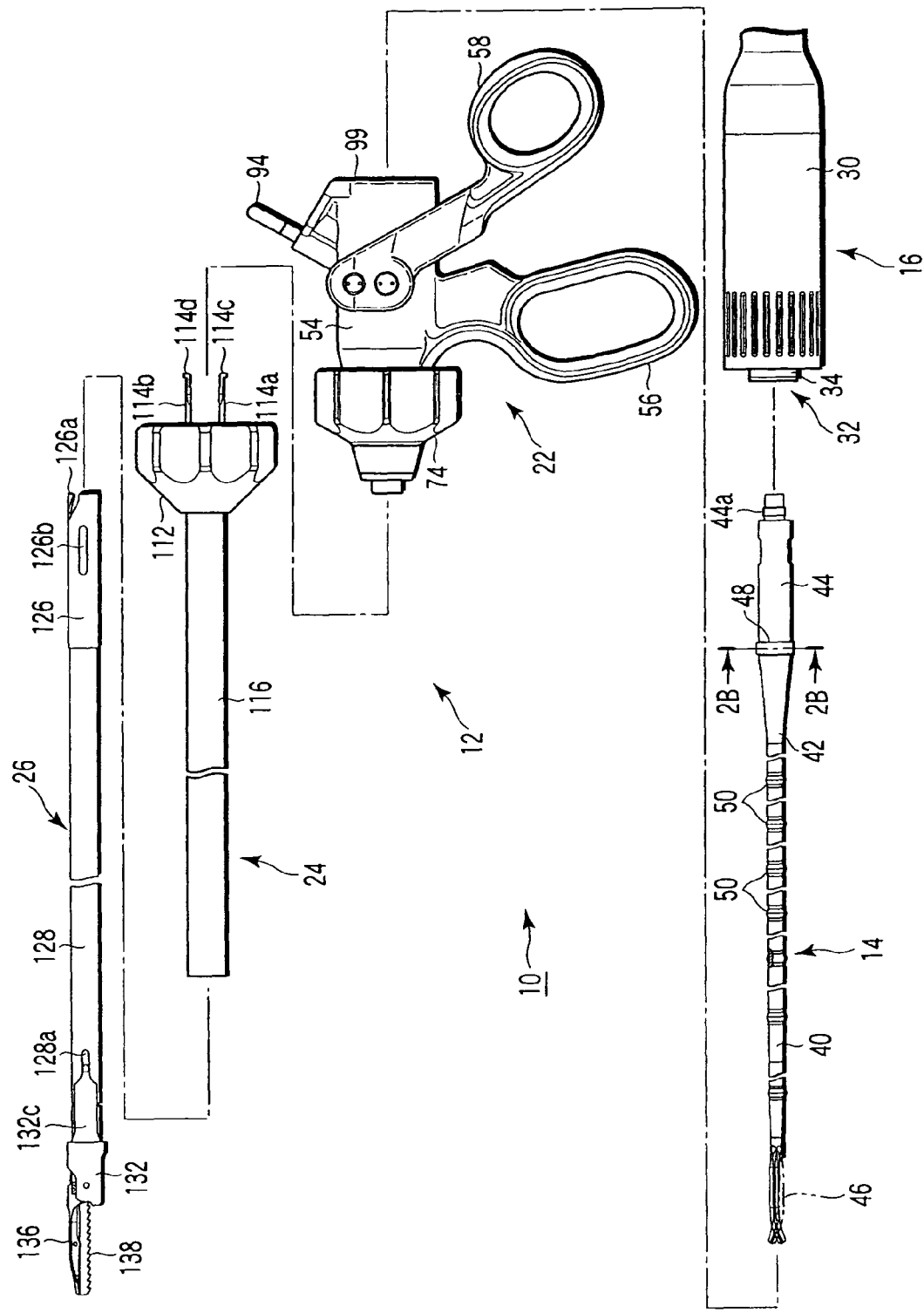
FIG. 2A is a schematic side view showing a state in which the ultrasonic treatment instrument according to the first embodiment is disassembled into a main body unit assembly, a probe, and a vibrator assembly and the main body unit assembly is further disassembled into a handle assembly, a sheath assembly, and a jaw assembly.
Figure 3:
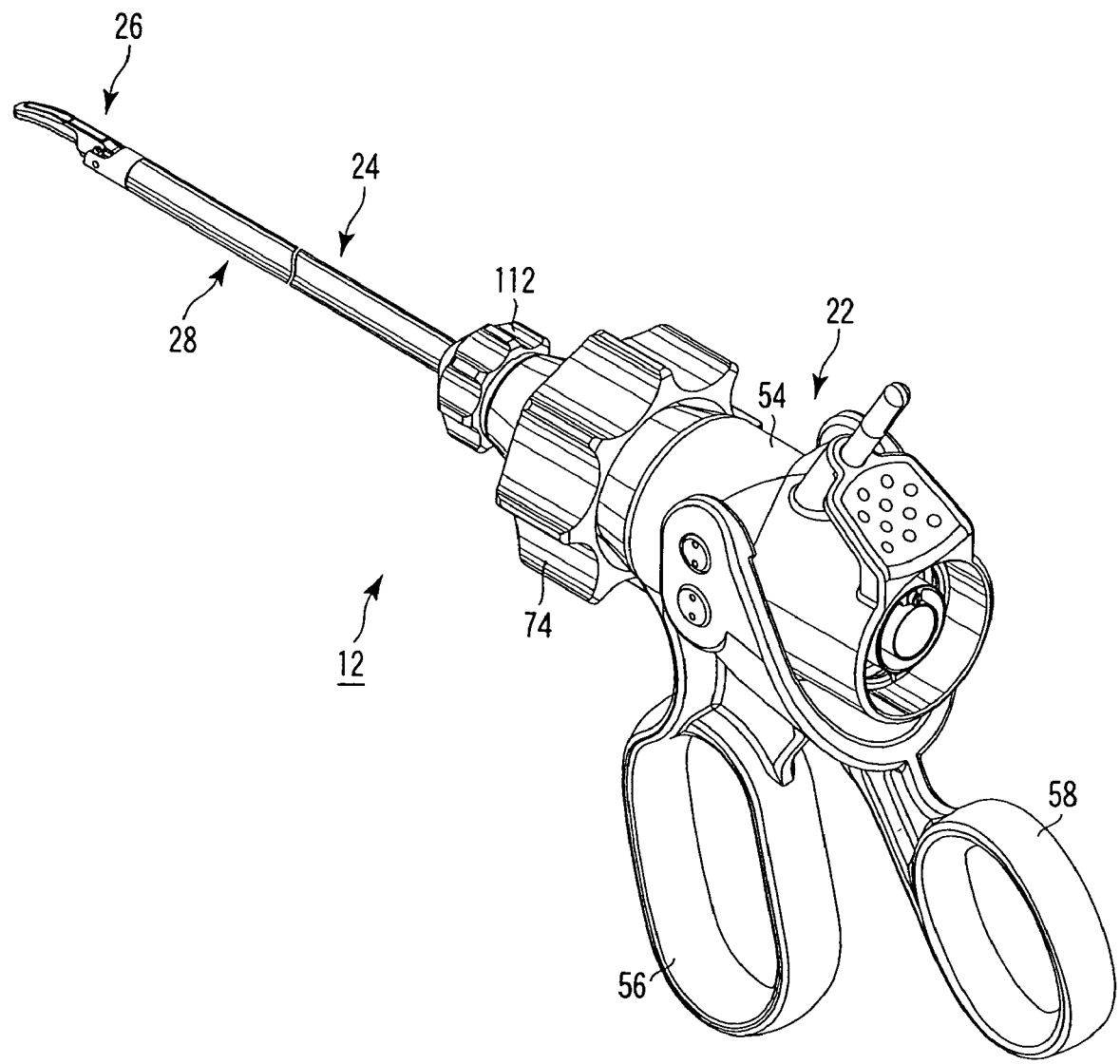
FIG. 3 is a perspective view of the main body unit assembly in the ultrasonic treatment instrument according to the first embodiment.

An ultrasonic treatment instrument (ultrasonic treatment apparatus) 10 shown in FIG. 1 includes a main body unit assembly 12, a probe 14, and a vibrator assembly 16. As shown in FIG. 2A, the main body unit assembly 12, the probe 14, and the vibrator assembly 16 are detachably attached to one another. The main body unit assembly 12 includes a handle assembly 22, a sheath assembly 24, and jaw assembly (treatment assembly) 26. The sheath assembly 24 and the jaw assembly 26 are detachably attached to the handle assembly 22. The jaw assembly 26 is detachably attached to the sheath assembly 24. When the sheath assembly 24 and the jaw assembly 26 are combined, an insertion portion unit assembly 28 (see FIG. 1) is assembled. When the insertion portion unit assembly 28 and the handle assembly 22 are combined, the main body unit assembly 12 is assembled as shown in FIG. 3.

As shown in FIGS. 1 and 2A, the probe 14 is detachably attached to the vibrator assembly 16. The vibrator assembly 16 is detachably attached to the handle assembly 22 of the main body unit assembly 12. Therefore, a unit assembly in which the probe 14 and the vibrator assembly 16 are combined is detachably attached to the main body unit assembly 12. That is, when the main body unit assembly 12, the probe 14, and the vibrator assembly 16 are combined, the ultrasonic treatment instrument 10 is assembled as shown in FIG. 1.

As shown in FIG. 2A, the vibrator assembly 16 includes a cylindrical vibrator cover 30 and an ultrasonic vibrator (not shown). The ultrasonic vibrator is incorporated in the vibrator cover 30 to generate ultrasonic vibration. The ultrasonic vibrator includes a horn (not shown) in a distal end portion thereof. The horn enlarges the amplitude of the generated vibration. A proximal end portion of the probe 14 is detachably attached to the horn. That is, the proximal end portion of the probe 14 is detachably attached to the distal end portion of the vibrator assembly 16.

The vibrator cover 30 includes an assembly coupling portion 32 in the distal end portion thereof. The assembly coupling portion 32 is detachably attached a vibrator connecting portion 99 (see FIG. 5) of a later-mentioned operation portion main body 54 of the main body unit assembly 12. A C-shaped engaging ring (C-ring) 34 which is partially cut is placed on an outer peripheral surface of the assembly coupling portion 32. As shown in FIG. 1, a power connecting cord 36 in which a vibrator plug (not shown) is provided is connected to a rear end portion of the vibrator cover 30.

Figure 2B:
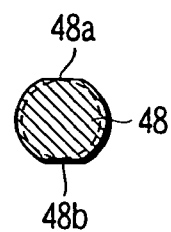
FIG. 2B is a sectional view taken on line 2B-2B in FIG. 2A of the probe in the ultrasonic treatment instrument according to the first embodiment.

As shown in FIG. 2A, the probe 14 includes a vibration transmission member (probe) 40, a horn portion 42, a maximum diameter portion 44, and a treatment portion 46. The vibration transmission member 40 is formed in a long straight rod. The horn portion 42 is arranged in the proximal end portion of the vibration transmission member 40. The maximum diameter portion 44 is arranged in the proximal end portion of the horn portion 42. The treatment portion 46 is arranged in the distal end portion of the vibration transmission member 40. An irregular sectional shape portion (first attaching-and-detaching mechanism) 48 is arranged in a coupling portion between the horn portion 42 and the maximum diameter portion 44. As shown in FIG. 2B, the irregular sectional shape portion 48 has a non-circular flange shape in section. The irregular sectional shape portion 48 positions the probe 14 with respect to parallel planes 90a and 90b (see FIG. 7C) of a later-mentioned positioning member (first attaching-and-detaching mechanism) 90.

As shown in FIG. 2A, plural ring-shaped support parts 50 are arranged in the outer peripheral surface of the vibration transmission member 40. The support parts 50 are formed by an elastic member such as a rubber material. The support parts 50 are arranged at positions of a node of a standingwave (hereinafter referred to as a vibration node) of the ultrasonic vibration transmitted toward the distal end side from the proximal end side of the outer peripheral surface of the vibration transmission member 40.

A mounting screw 44a is arranged in the proximal end portion of the maximum diameter portion 44. The mounting screw 44a is screwed into a threaded hole portion of a probe mounting portion at the distal end portion of the horn of the vibrator assembly 16. Therefore, the probe 14 and the vibrator assembly 16 can integrally be combined. The horn portion 42 located between the maximum diameter portion 44 and the vibration transmission member 40 enlarges the amplitude of the ultrasonic vibration transmitted from the vibrator assembly 16. The vibration transmission member 40 transmits the ultrasonic vibration, enlarged by the horn portion 42, toward the treatment portion 46.

The treatment portion 46 is provided in order to come into contact with the biological tissue to perform the treatment. The treatment portion 46 is formed in an asymmetrical shape, in which the treatment portion 46 is curved toward a direction shifted from a center axis of the vibration transmission member 40, e.g., in an arc shape. The shape of the treatment portion 46 will be described later. An appropriate shape is used as the shape of the treatment portion 46 for any purpose (see FIGS. 16A and 17).

Figure 4:
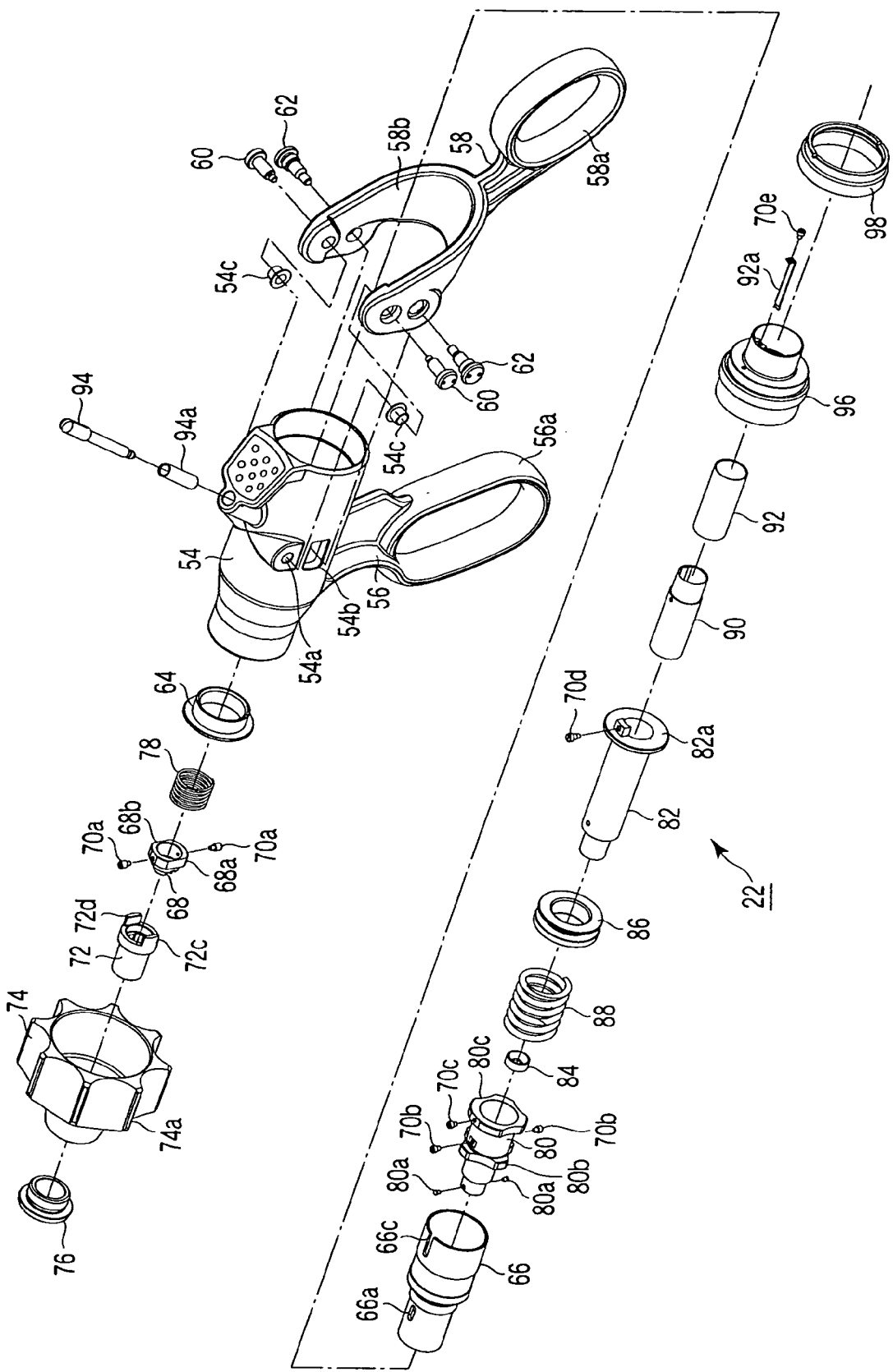
FIG. 4 is an exploded perspective view of the handle assembly of the main body unit assembly in the ultrasonic treatment instrument according to the first embodiment.

As shown in FIG. 4, the handle assembly 22 includes an operation portion main body 54 having an insulating property. The operation portion main body 54 is formed in a substantially cylindrical housing. A fixed handle 56 is integrally formed in the outer peripheral surface of the operation portion main body 54. A finger through-hole 56a through which any finger except for a thumb can selectively be passed is made in an operation end portion (lower end portion) of the fixed handle 56. A movable handle 58 which is rotatable to the fixed handle 56 is arranged in the operation portion main body 54. A finger through-hole 58a through which the thumb of the same hand can selectively be passed is made in an operation end portion (lower end portion) of the movable handle 58.

A pair of fulcrum pin receiving portions 54a and a pair of action pin working windows 54b are formed in the outer peripheral surface of the operation portion main body 54. Because the action pin working window 54b is pierced through the a wall portion of the operation portion main body 54, the operation portion main body 54 is communicated with a bore of the operation portion main body 54 from a side portion (see FIG. 7C). A coupling portion 58b branched in a Y-shape is formed in an upper end portion of the movable handle 58. Fulcrum pins 60 arranged in the fulcrum pin receiving portion 54a are mounted in the upper end portion of the movable handle 58. The fulcrum pins 60 are coupled to the operation portion main body 54 on the upper side in FIG. 5 of an axis line in which a later-mentioned insulating tube 116 of the sheath assembly 24 is mounted to the handle assembly 22. The fulcrum pins 60 are mounted to the fulcrum pin receiving portion 54a through a collar (insulating cap) 54c, formed by a low friction coefficient member, which smoothly rotates the movable handle 58. Therefore, the movable handle 58 can be opened and closed with respect to the fixed handle 56.

An action pin 62 arranged in the action pin working windows 54b is mounted in the upper end portion of the movable handle 58 and below the fulcrum pin 60. An end portion of the action pin 62, arranged inside the operation portion main body 54, is provided in a pin receiving portion 86a of a later-mentioned slider 86. Therefore, when the movable handle 58 is opened and closed on the fulcrum pin 60 with respect to the fixed handle 56, the slider 86 is caused to proceed and retreat by the action pin 62.

Figure 5:
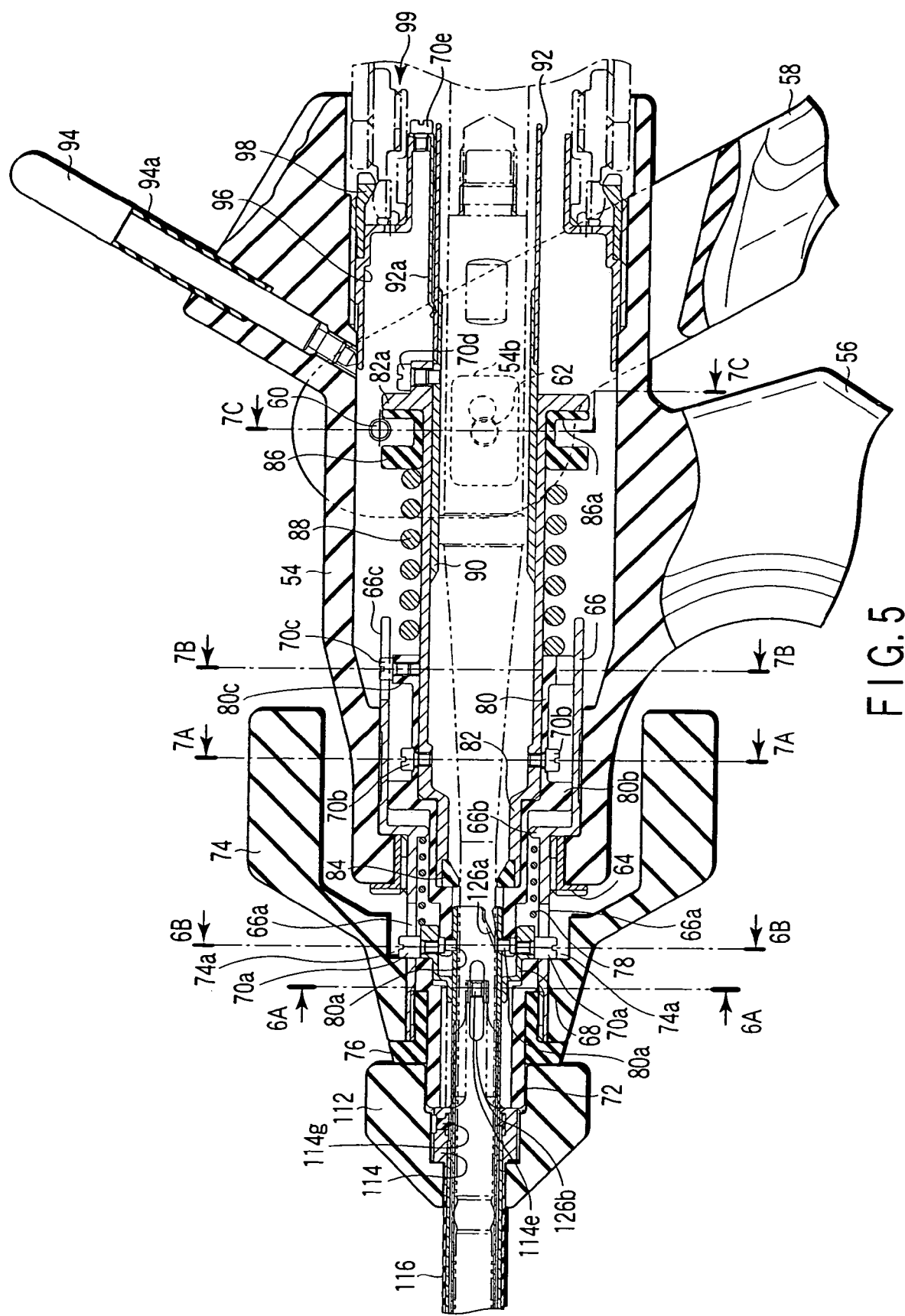
FIG. 5 is a longitudinal sectional view of the handle assembly of the main body unit assembly in the ultrasonic treatment instrument according to the first embodiment.

As shown in FIGS. 4 and 5, a fixing ring 64 is mounted to an edge portion in an inner peripheral surface of the distal end portion of the operation portion main body 54. An internal thread portion is formed in the inner peripheral surface of the fixing ring 64. A cylindrical rotating hook member 66 is arranged inside the fixing ring 64. The rotating hook member 66 includes a small diameter portion located in the distal end portion, a large diameter portion located in the proximal end portion, and a step between the small diameter portion and the large diameter portion. An external thread portion is formed at a position close to the step of the outer peripheral surface of the small diameter portion in the distal end portion of the rotating hook member 66. The external thread portion of the rotating hook member 66 is screwed in the internal thread portion of the fixing ring 64.

Figure 6A:
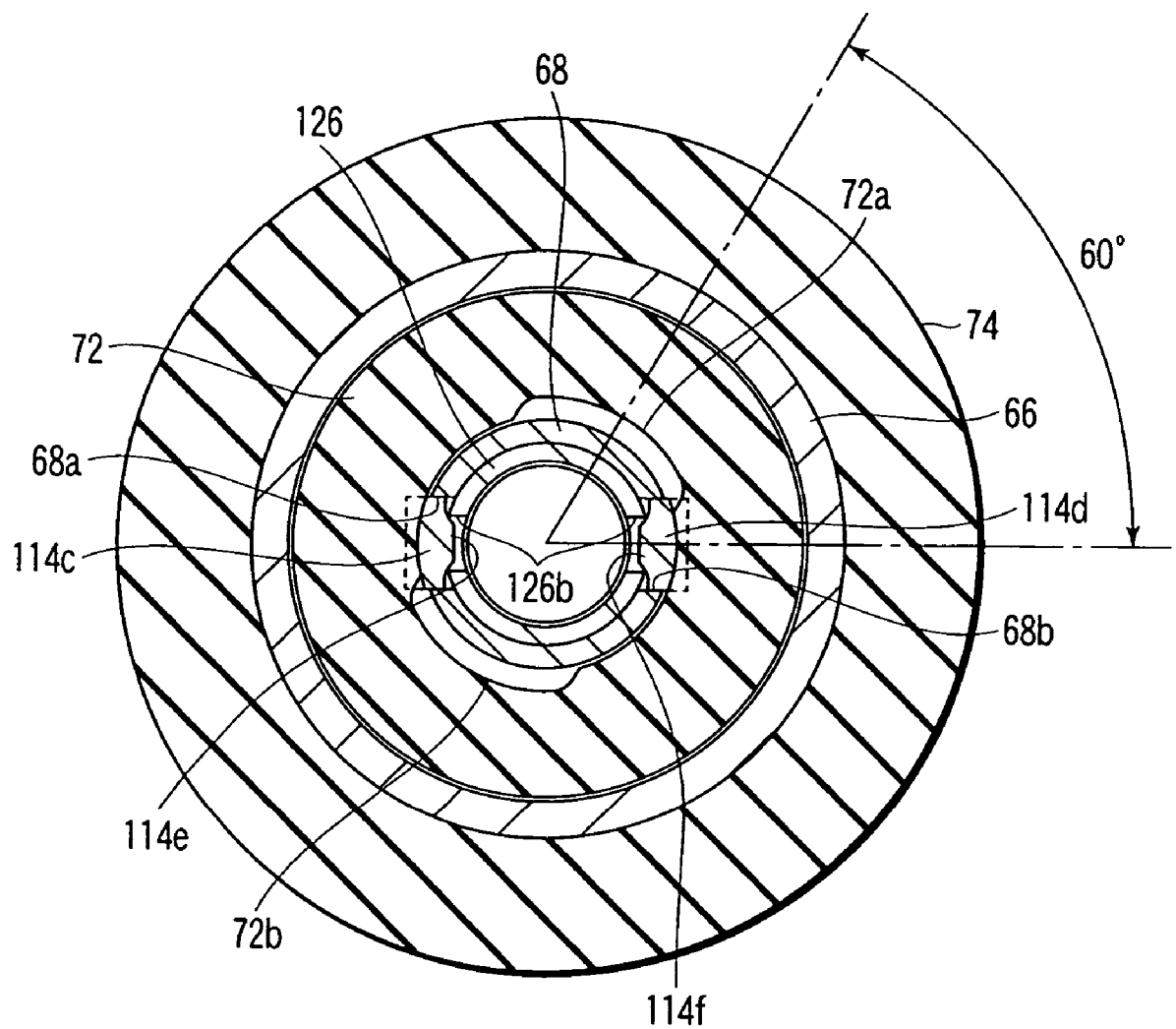
FIG. 6A is a sectional view taken on line 6A-6A in FIG. 5.

In the outer peripheral surface of the small diameter portion of the rotating hook member 66, a pair of long holes 66a facing each other is made along the axial direction of the rotating hook member 66. The long holes 66a are made on the distal end side past the external thread portion. A cylindrical rotating fixing member 68 which is slidable in the axial direction of the rotating hook member 66 is arranged inside the small diameter portion of the rotating hook member 66. A pair of first pins 70a is arranged in the rotating fixing member 68 while pierced through the long holes 66a of the rotating hook member 66 respectively. That is, the first pins 70a are held in the long holes 66a of the rotating hook member 66 respectively. This enables the rotating fixing member 68 to be moved along a longitudinal axis of the long hole 66a of the rotating hook member 66 by the first pin 70a. As shown in FIG. 6A, a pair of slit portions (first mounting mechanism) 68a and 68b facing each other is formed in the distal end portion of the rotating fixing member 68.

In the outside of the rotating fixing member 68, a cylindrical sheath connecting member 72 is arranged inside the small diameter portion of the rotating hook member 66. The sheath connecting member 72 is arranged on the distal end portion side past the position where the first pin 70a is arranged. That is, the cylindrical sheath connecting member 72 and the rotating hook member 66 are arranged and fixed outside the distal end portion of the rotating fixing member 68.

As shown in FIG. 6A, in the inner peripheral surface of the distal end portion of the sheath connecting member 72, slits 72a and 72b are formed in an opening edge portion having a circular shape in section while being located at the positions facing each other. The slits 72a and 72b facing each other are formed at the positions where the slits 72a and 72b are inclined by 60° with respect to the center of the sheath connecting member 72 respectively. As shown in FIG. 4, a pair of arms 72c and 72d is formed in the proximal end portion of the sheath connecting member 72 in order to position the rotating fixing member 68 with respect to the hole in the inner peripheral surface of the sheath connecting member 72 during the assembly.

Figure 6B:
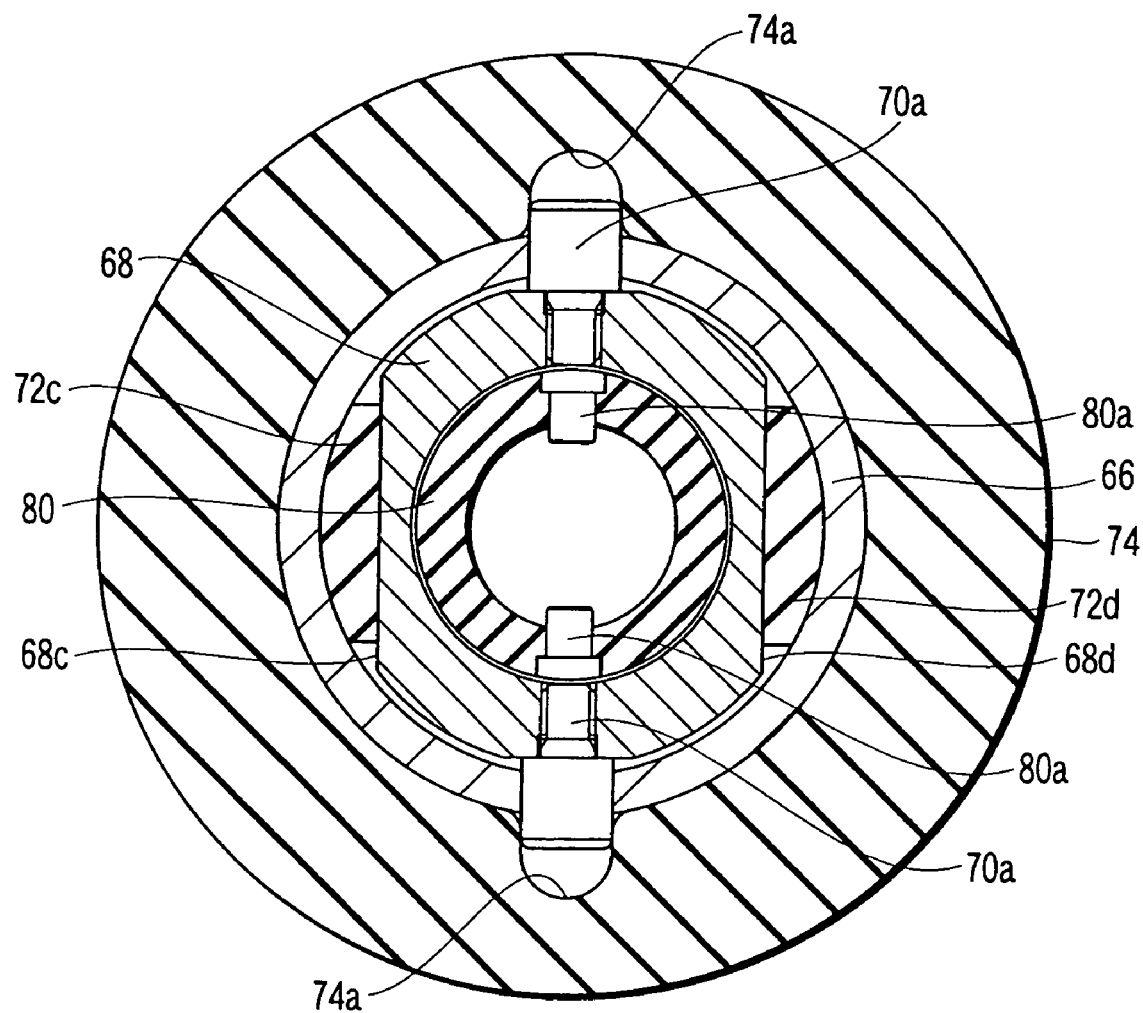
FIG. 6B is a sectional view taken on line 6B-6B in FIG. 5.

As shown in FIG. 5, the sheath connecting member 72 is positioned by causing a part of a proximal end surface of the sheath connecting member 72 to abut on the rotating fixing member 68. As shown in FIG. 6B, parallel planes 68c and 68d facing each other are formed in the outer peripheral surface of the proximal end portion of the rotating fixing member 68. Planes abutting on the parallel planes 68c and 68d are formed in the inner peripheral surface of the proximal end portions of the arms 72c and 72d of the sheath connecting member 72 respectively. The outer peripheral surfaces of the proximal end portions of the arms 72c and 72d of the sheath connecting member 72 are formed in the shape along the inner peripheral surface shape of the rotating hook member 66.

As shown in FIGS. 4 and 5, a ring-shaped or cylindrical rotating knob 74 which includes a slip stopper 74a in the outer peripheral surface is mounted in the outer peripheral surface of the rotating hook member 66 while being slidable in the axial direction with respect to the rotating hook member 66. As shown in FIG. 6B, a pair of pin receiving portions 74a engaging the first pins 70a is formed inside the rotating knob 74. Therefore, the rotating knob 74 is fixed while the rotation of the rotating knob 74 is prevented with respect to the rotating fixing member 68 and the rotating hook member 66. That is, when the rotating knob 74 is rotated, the rotating hook member 66 is also rotated by following the rotation of the rotating knob 74.

A ring-shaped fixing member 76 is arranged at the position where the distal end surfaces of the rotating hook member 66 and rotating knob 74 are covered. The external tread portion is formed in the outer peripheral surface of the fixing member 76. The internal thread portion which can be screwed on the external thread portion in the outer peripheral surface of the fixing member 76 is formed in the inner peripheral surface of the rotating hook member 66. Therefore, the fixing member 76 and the rotating hook member 66 are screwed each other by the thread portions.

As shown in FIG. 5, a flange portion 66b protruded toward a radially inward direction is formed in the inner peripheral surface of the step of rotating hook member 66. A coil spring 78 is arranged between the proximal end portion of the rotating fixing member 68 and the flange portion 66b of the rotating hook member 66. In the pair of first pins 70a, the rotating fixing member 68 is biased onto the distal end portion side of the rotating hook member 66. Therefore, usually the first pins 70a are arranged at the distal end of the long holes 66a of the rotating hook member 66 respectively. The rotating knob 74 also engages the pair of first pins 70a by the pin receiving portion 74a. Therefore, the proximal end of the position where the rotating knob 74 is mounted is aligned with the distal end of the long hole 66a of the rotating hook member 66. Accordingly, when the rotating knob 74 is pulled toward the proximal end side with a force more than a capacity of a coil spring 78, the rotating knob 74 and the rotating fixing member 68 slide along the axial direction of the long hole 66a within a length range of the long hole 66a of the rotating hook member 66.

A cylindrical drive pipe connecting member (drive shaft connecting member) 80 is arranged on the proximal end side of the rotating fixing member 68 while being slidable in the axial direction with respect to the rotating hook member 66. A pair of drive pipe connecting pins (first mounting mechanism) 80a is arranged in the distal end portion of the drive pipe connecting member 80. The drive pipe connecting pins 80a are protruded to the radially inward direction, and the drive pipe connecting pins 80a can engage a later-mentioned pair of cam grooves (second mounting mechanism) 126a of the jaw assembly 26. A slider receiving member 82 is connected onto the rear end side of the drive pipe connecting member 80 by a pair of second pins 70b. The distal end portion of the slider receiving member 82 is arranged inside the drive pipe connecting member 80. A protective ring 84 made of a low-friction insulating material such as PTFE is mounted inside the distal end portion of the slider receiving member 82 such that the probe 14 prevent to come into contact with a surrounding rigid portion when the probe 14 is assembled to the main body unit assembly 12.

Figure 7A:
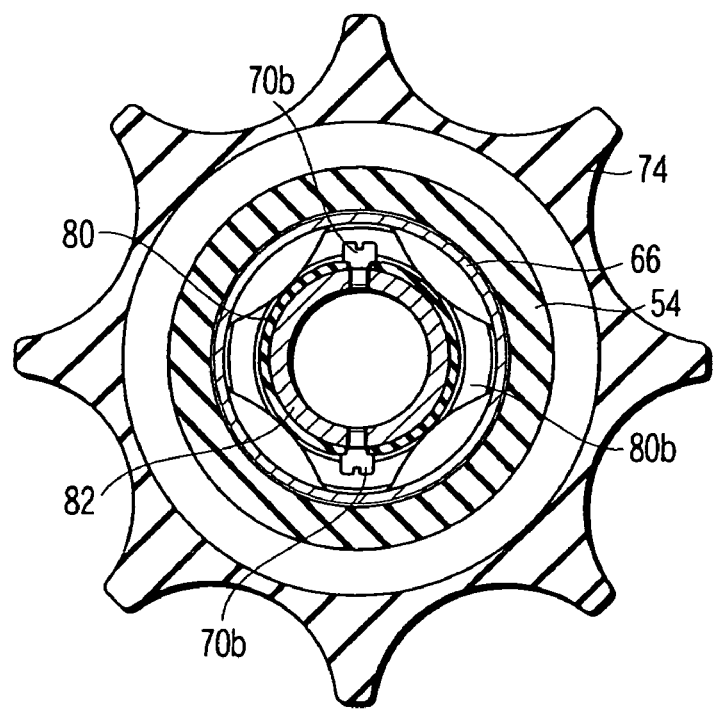
FIG. 7A is a sectional view taken on line 7A-7A in FIG. 5.
Figure 7B:
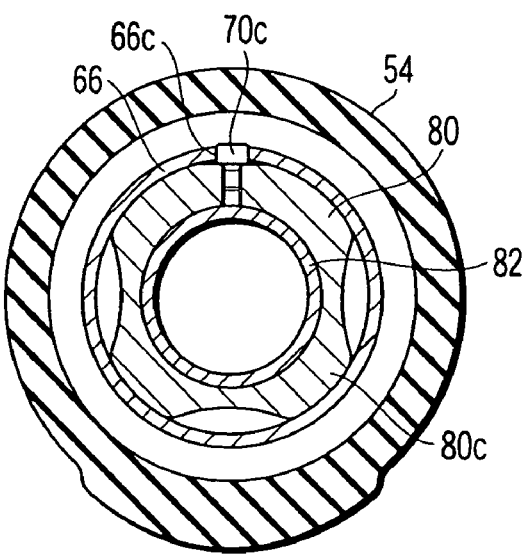
FIG. 7B is a sectional view taken on line 7B-7B in FIG. 5.

As shown in FIGS. 7A and 7B, flange portions 80b and 80c are formed in an intermediate portion and the rear end portion of the drive pipe connecting member 80. The flange portions 80b and 80c are protruded toward a radially outward direction. In the flange portions 80b and 80c, several arc notches are formed in the outer periphery. Therefore, in the case where the handle assembly 22 is cleaned, a cleaning solution can easily reach a gap between the flange portions 80b and 80c and the distal end sides and rear end sides of the flange portions 80b and 80c, and the cleaning solution can easily be discharged. The total mass of the drive pipe connecting member 80 can therefore be reduced.

A third pin 70c is attached to the flange portion 80c of the drive pipe connecting member 80. The third pin 70c engages a slit 66c located on the rear end side of the rotating hook member 66. The slit 66c extends in the axial direction, and the third pin 70c is slidable along the slit 66c in the axial direction. On the other hand, the third pin 70c is rotated in the rotation direction about the axis by following the rotation of the rotating hook member 66. In the rotating hook member 66 and the drive pipe connecting member 80, the outer periphery of the drive pipe connecting member 80 abuts on the flange portion 66b of the rotating hook member 66. The outer peripheries of the flange portions 80b and 80c abut on the inner peripheries of the rotating hook member 66. Therefore, the drive pipe connecting member 80 is slidable in the axial direction while generation of looseness or the like is suppressed.

A flange portion 82a protruded toward the radially outward direction is formed in the proximal end portion of the slider receiving member 82. The substantially ring-shaped slider 86 having the insulating property is arranged in the outer peripheral surface of the slider receiving member 82. The slider 86 is movable along the axial direction of the slider receiving member 82 between the flange portion 80c of the drive pipe connecting member 80 and the flange portion 82a of the slider receiving member 82. A groove-shaped pin receiving portion 86a is formed in the outer peripheral surface of the slider 86. The end portion of the action pin 62 of the movable handle 58 is arranged in the pin receiving portion 86a.

A coil-shaped driving force restriction spring 88 is arranged outside the slider receiving member 82. The driving force restriction spring 88 is arranged between the flange portion 80c of the drive pipe connecting member 80 and the slider 86 while the length of the driving force restriction spring 88 is shorter than a free length. The slider 86 is biased at constant force to the proximal end-side flange portion 82a of the slider receiving member 82. Therefore, when the movable handle 58 is opened and closed with respect to the fixed handle 56, the slider 86, the slider receiving member 82, and the drive pipe connecting member 80 proceed and retreat integrally, in the case where the force transmitted from the action pin 62 to the distal end side in the axial direction is not more than the capacity of the driving force restriction spring 88. In the case where the force transmitted from the action pin 62 to the distal end side in the axial direction is more than the capacity of the driving force restriction spring 88, the slider 86 proceeds and retreats along the outer peripheral surface of the slider receiving member 82 against/according to the biasing force of the driving force restriction spring 88, which prevents the transmission of a force more than a predetermined amount to the distal end side in the axial direction.

Figure 7C:
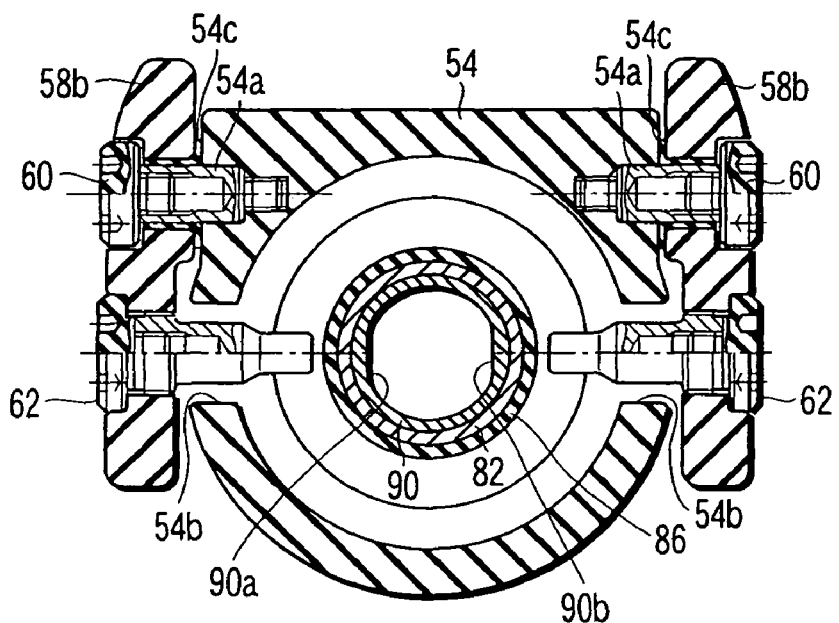
FIG. 7C is a sectional view taken on line 7C-7C in FIG. 5.

A cylindrical positioning member (first attaching and detaching mechanism) 90 is arranged in the inner peripheral surface of the slider receiving member 82. The probe 14 is positioned in the positioning member 90 having an electroconductive property. The positioning member 90 is fixed by a fourth pin 70d on the proximal end portion side past the flange portion 82a of the slider receiving member 82. As shown in FIG. 7C, parallel planes 90a and 90b facing each other are formed in the inner peripheral surface of the positioning member 90. Therefore, the parallel planes 48a and 48b of the irregular sectional shape portion 48 of the probe 14 shown in FIG. 2B are mounted while positioned at predetermined positions.

As shown in FIGS. 4 and 5, the distal end portion of an electroconductive contact pipe 92 is fitted to the outer peripheral surface of the proximal end portion of the positioning member 90.

A high-frequency connecting pin 94 connected to a high-frequency power source (electric cautery power source) is attached to the upper portion of the proximal end portion of the operation portion main body 54 through an insulating cover 94a while inclined rearward. The insulating cover 94a is provided to enhance electrical safety in the case where the high-frequency connecting pin 94 is incompletely arranged in the high-frequency power source.

While the lower end portion of the high-frequency connecting pin 94 abuts on the inner peripheral surface of the proximal end portion of the operation portion main body 54, a vibrator assembly guide 96 is mounted on the inner peripheral surface of the proximal end portion of the operation portion main body 54 while electrically connected. In the outer peripheral surface of the proximal end portion of the vibrator assembly guide 96, a C-ring receiving member 98 which receives the engaging ring 34 shown in FIG. 2 is screwed to the inner peripheral surface of the operation portion main body 54. Therefore, a vibrator connecting portion 99 which the assembly coupling portion 32 of the vibrator assembly 16 engages is formed by the C-ring receiving member 98 and the guide 96.

A connector 92a having an L-shape in section is mounted to the proximal end portion of the guide 96 by a fifth pin 70e. The connector 92a is in contact with the outer peripheral surface of the contact pipe 92. The connector 92a is biased with a constant force while elastically deformed. The distal end portion of the connector 92a is formed in a U-shape in section, and a U-shaped bottom portion is designed to be located inside the outer peripheral surface of the contact pipe 92. Therefore, the connector 92a is in point contact with the outer peripheral surface of the contact pipe 92 while elastically deformed outward. In the above configuration, for example, in the case where the probe 14 is mounted in the operation portion main body 54 of the handle assembly 22, a member protruded toward the radially inward direction is not provided in the contact pipe 92 and the positioning member 90. Therefore, in this case, the distal end portion of the treatment portion 46 of the probe 14 or the like can easily and securely be mounted without catching the distal end portion of the treatment portion 46 on the contact pipe 92 or the positioning member 90.

The high-frequency connecting pin 94 is electrically connected to the contact pipe 92 by the connector 92a of the vibrator assembly guide 96. The contact pipe 92 and the positioning member 90 are fitted to each other. Therefore, the high-frequency connecting pin 94 is electrically connected to the positioning member 90.

Thus, the handle assembly 22 is configured (see FIG. 2A).

As shown in FIG. 8, the sheath assembly 24 includes a knob 112, a sheath assembly connecting member 114, an insulating tube 116, a long pipe 118, and a end cover 120.

A pair of bifurcated fixed arms 114a and 114b is extended from the proximal end portion of the sheath assembly connecting member 114. In the proximal end portion of the fixed arms 114a and 114b, fixed portions (fourth mounting mechanism) 114c and 114d are formed as an outward protrusion portion protruded toward the radially outward direction. The fixed portions 114c and 114d can engage and disengage the sheath connecting member 72 of the handle assembly 22.

As shown in FIGS. 6A and 8, inward protrusion portions 114e and 114f protruded toward the radially inward direction are formed in the proximal end portions of the fixed arms 114a and 114b. As shown in FIG. 8, a ring-shaped packing 114g is mounted inside the sheath assembly connecting member 114. The packing 114g is brought into close contact with the outer peripheral surface of a later-mentioned jaw assembly connecting member 126 (see FIG. 9) of the jaw assembly 26 to establish air tight. Therefore, in the assembled state, for example, a pneumoperitoneum gas used in a surgical operation with an endoscope is prevented from leaking to the sides of the handles 56 and 58 from the gap between the sheath assembly 24 and the jaw assembly 26.

As shown in FIG. 8, the long pipe 118 is mounted on the distal end side of the sheath assembly connecting member 114. A pair of cam grooves (second recess) 118a is formed in the distal end portion of the long pipe 118. The cam grooves 118a are formed in the substantially L-shape. Therefore, the cam groove 118a includes a region which is extended in the axial direction from the distal end toward the proximal end side of the long pipe 118 and a region which is orthogonal to the end portion on the proximal end side of the former region while extended to the position inclined about 60° with respect to the axis center of the long pipe 118. Outward protrusion portions (third mounting mechanism) 132i and 132j (see FIGS. 8 and 10B) of arms 132c and 132d of a later-mentioned jaw support member (action portion support member) 132 in the jaw assembly 26 (see FIG. 9) engage the cam grooves (fifth mounting mechanism) 118a. The end cover 120 with which the cam grooves 118a are covered is arranged in the outer periphery of the distal end portion of the long pipe 118. The distal end surface of the end cover 120 includes an edge portion protruded toward the radially outward direction.

Figure 10A:
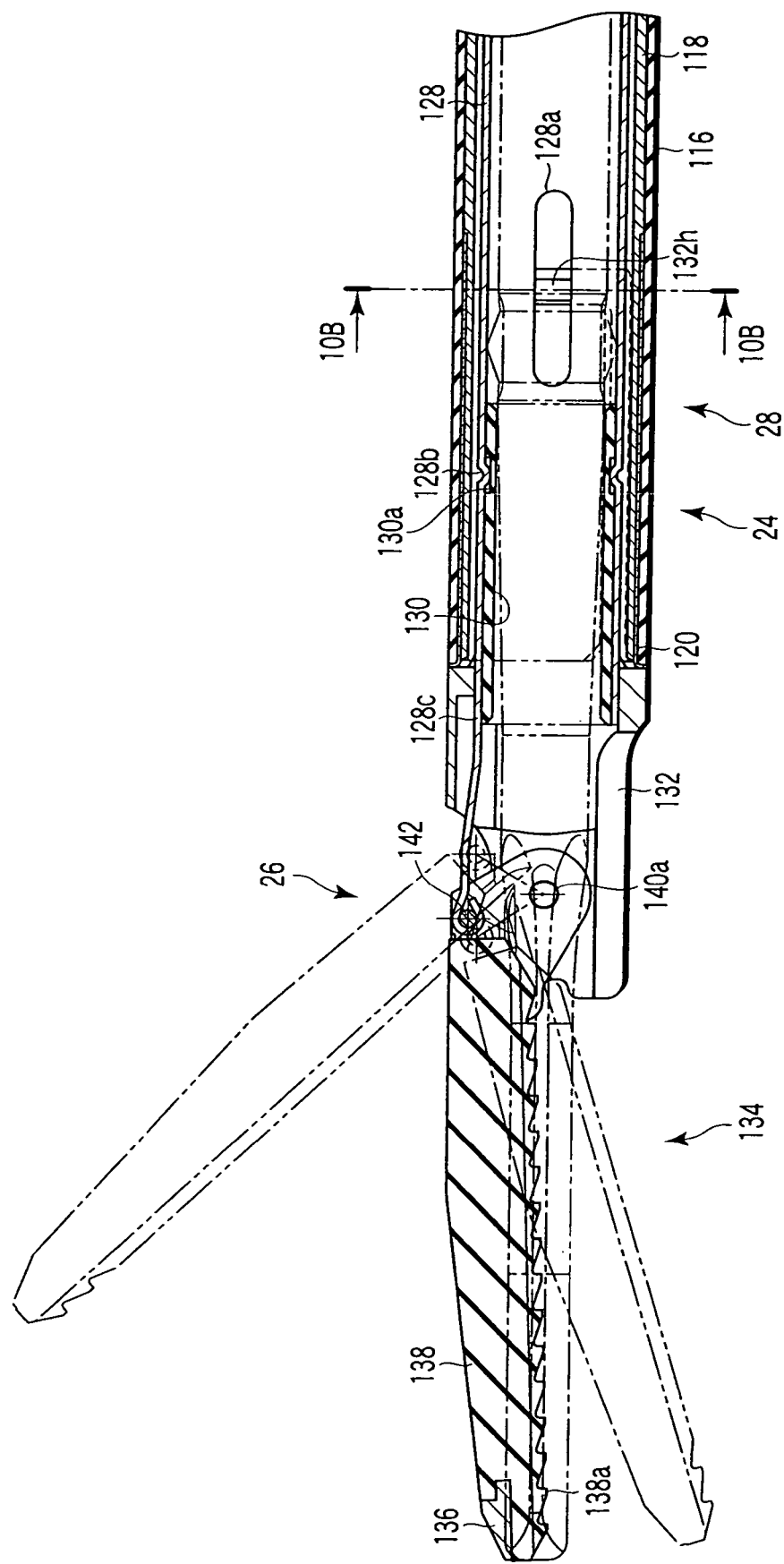
FIG. 10A is a longitudinal sectional view showing a distal end portion of the main body unit assembly in the ultrasonic treatment instrument according to the first embodiment.

The external thread portion is provided in the outer periphery of the sheath assembly connecting member 114. The external thread portion is screwed in the internal thread portion located in the inner peripheral surface of the cylindrical knob 112. A slip stopper 112a is formed in the outer peripheral surface of the knob 112. The outer peripheries of the end cover 120 and long pipe 118 is coated with the insulating tube 116. As shown in FIG. 10A, the distal end side of the insulating tube 116 abuts on the edge portion located at the distal end of the end cover 120. As shown in FIG. 5, the proximal end portion of the insulating tube 116 is extended to the inner peripheral surface of the knob 112. Thus, the sheath assembly 24 is configured (see FIG. 2A).

Figure 9:
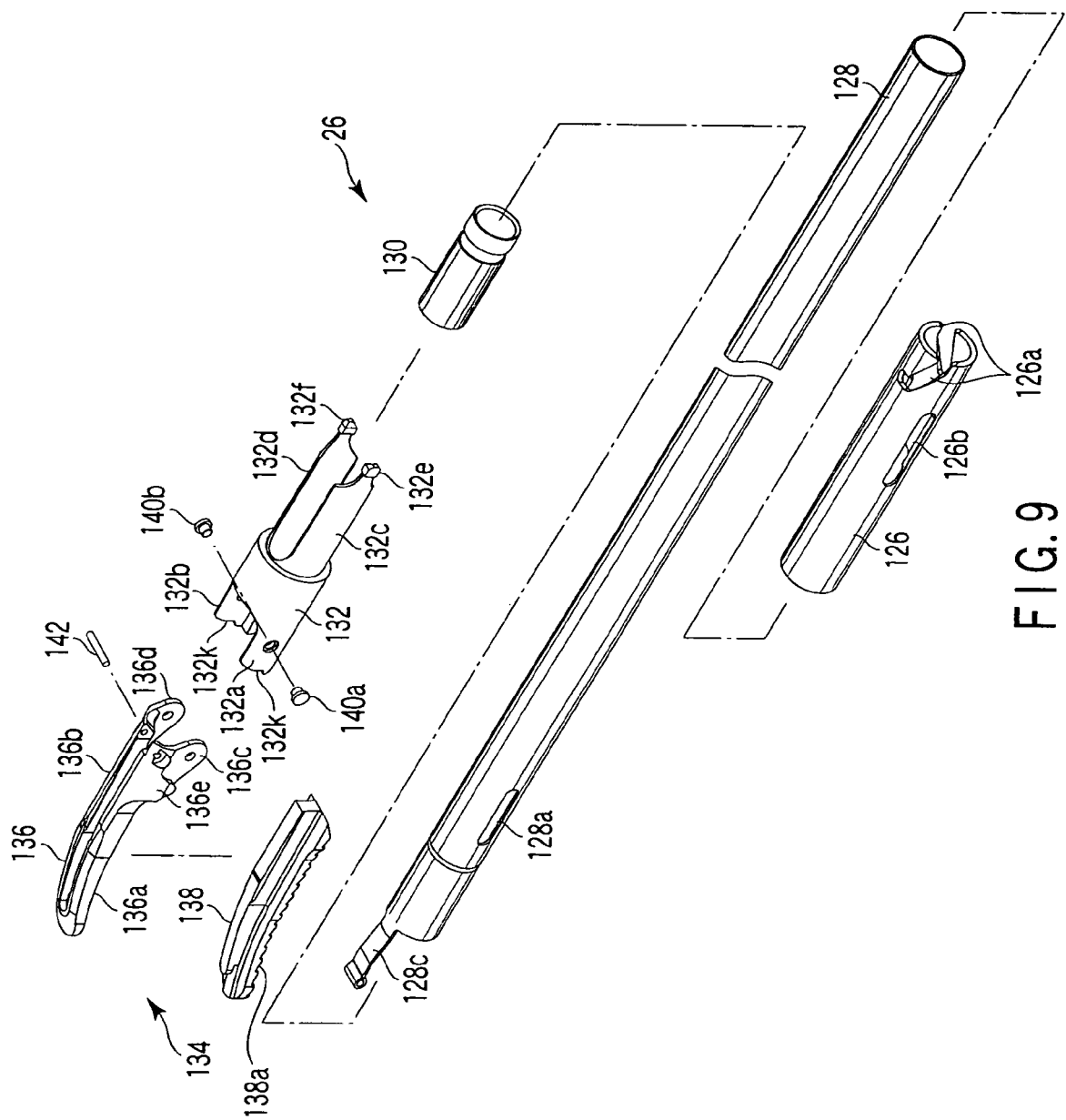
FIG. 9 is an exploded perspective view of the jaw assembly of the main body unit assembly in the ultrasonic treatment instrument according to the first embodiment.

As shown in FIG. 9, the jaw assembly 26 includes a jaw assembly connecting member 126, a drive pipe (drive shaft) 128, a protective member 130, a jaw support member 132, and a distal-end action portion 134.

Figure 10B:
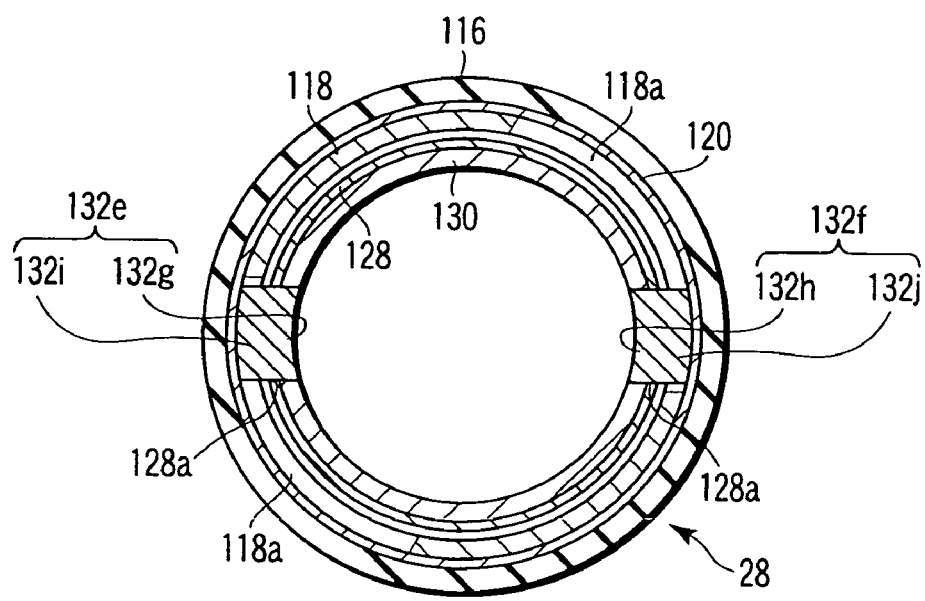
FIG. 10B is a transverse sectional view taken along line 10B-10B in FIG. 10A of the distal end portion of the main body unit assembly in the ultrasonic treatment instrument according to the first embodiment.

The jaw support member 132 is formed in the cylindrical shape. The jaw support member 132 includes a pair of arms 132a and 132b and a pair of arms 132c and 132d in the distal end portion and the proximal end portion respectively. The arms 132a and 132b on the distal end portion side are set at first arms, and the arms 132c and 132d on the proximal end portion side are set at second arms. Protrusion portions 132e and 132f are formed in the proximal end portion of the second arms 132c and 132d. As shown in FIG. 10B, the protrusion portions 132e and 132f include inward protrusion portions 132g and 132h and outward protrusion portions 132i and 132j respectively. The inward protrusion portions 132g and 132h are protruded toward the inward direction of the second arms 132c and 132d of the jaw support member 132, and the outward protrusion portions 132i and 132j are protruded toward the outward direction of the second arms 132c and 132d. The inward protrusion portions 132g and 132h are engaged in later-mentioned long holes (first recess) 128a of the drive pipe 128. On the other hand, the outward protrusion portions 132i and 132j are engaged in the cam grooves 118a (see FIG. 8) of the distal end portion of the long pipe 118 in the sheath assembly 24.

The jaw assembly connecting member 126 is formed in the cylindrical shape. A pair of cam grooves 126a is formed in the proximal end portion of the connecting member 126. Each of the cam grooves 126a is formed by a region obliquely extended from the proximal end of the jaw assembly connecting member 126 toward the distal end side and a region extended from the end portion on the distal end side of the former region toward the direction orthogonal to the axial direction of the connecting member 126. The drive pipe connecting pin 80a (see FIG. 5) of the drive pipe connecting member 80 of the handle assembly 22 can engage and disengage the cam groove 126a. A pair of long holes 126b is formed along the axial direction of the connecting member 126 while located nearer the proximal end portion of the jaw assembly connecting member 126. The inward protrusion portions 114e and 114f (see FIG. 8) of the fixed arms 114a and 114b in the connecting member 114 of the sheath assembly 24 can engage and disengage the long holes 126b respectively.

The outer peripheral surface of the proximal end portion of the drive pipe 128 is fixed to the inner peripheral surface of the distal end portion of the jaw assembly connecting member 126 by bonding, welding, or the like. The distal end portion of the drive pipe 128 is arranged inside the jaw support member 132 while being slidable in the longitudinal direction. A pair of long holes 128a is formed along the axial direction of the drive pipe 128 while located near the distal end portion of the drive pipe 128. The inward protrusion portions 132g and 132h of the second arms 132c and 132d of the jaw support member 132 are fitted in the long holes 128a from the outside as described above. Therefore, the drive pipe 128 is slidable in the longitudinal direction while fixed in the rotation direction with respect to the jaw support member 132.

As shown in FIG. 10A, an inward protrusion portion 128b protruded toward the radially inward direction is formed in the inner peripheral surface of the drive pipe 128 while located slightly nearer the distal end portion in relation to the long hole 128a. The outer peripheral surface of the cylindrical protective member (cylindrical member) 130 is fixed to the inner peripheral surface of the distal end portion of the drive pipe 128 by, e.g., bonding. An annular groove (groove portion) 130a is formed in the outer peripheral surface of the protective member 130. The inner protrusion portion 128b of the drive pipe 128 engages the annular groove 130a.

A pin receiving portion 128c is formed in the distal end portion of the drive pipe 128. The pin receiving portion 128c is extended from the distal end edge portion of the drive pipe 128 and is integrated with the distal end side of the drive pipe 128. That is, a part of the pin receiving portion 128c is extended in the tab shape from the distal end edge portion of the drive pipe 128. The distal end portion of the pin receiving portion 128c is rounded toward the radially inward direction of the drive pipe 128. Therefore, while a later-mentioned coupling pin 142 is arranged in the pin receiving portion 128c, the coupling pin 142 is arranged in a jaw main body 136, which couples the drive pipe 128 and the jaw main body 136.

As shown in FIG. 9, the distal-end action portion 134 includes the jaw main body 136 whose proximal end portion is formed in the substantially arch shape and a grip member 138 which grips a subject (biological tissue). The jaw main body 136 includes a pair of arms 136a and 136b. The pair of arms 136a and 136b is coupled in the distal end portion and bifurcated in the proximal end portion. Therefore, a predetermined gap is formed in the proximal end portion of the jaw main body 136. The grip member 138 is made of a material such as PTFE, which has a heat-resistant property and decreases frictional resistance to a member with which the grip member comes into contact. A slip stopper tooth portion (grip surface) 138a is formed in the sawtooth shape in the grip member 138. In the slip stopper tooth portion 138a, plural slip stopper teeth are vertically provided on the grip surface side which grips the biological tissue of a solidifying or cutting target. The grip surface 138a of the grip member 138 can grip the biological tissue which is of the solidifying or cutting target without slippage of the biological tissue. A projection portion 138b fitted between the pair of arms 136a and 136b of the jaw main body 136 is formed on the opposite side to the grip surface 138a of the grip member 138. Therefore, as shown in FIGS. 11B and 11C, the grip member 138 is mounted by fitting, bonding for example, the grip member 138 in the gap of the jaw main body 136 to bond the grip member 138.

As shown in FIG. 9, leg portions 136c and 136d are formed in the proximal end portions of the arms 136a and 136b of the jaw main body 136. The first arms 132a and 132b of the jaw support member 132 and the leg portions 136c and 136d of the proximal end portions of the arms 136a and 136b of the jaw main body 136 are coupled with pivot studs 140a and 140b respectively. That is, the jaw main body 136 is coupled to the jaw support member 132 by the pivot studs 140a and 140b. Therefore, the jaw main body 136 is rotatable with respect to the distal end portion of the jaw support member 132.

In the proximal end portions of the arms 136a and 136b of the jaw main body 136, pin hole insertion portions are formed on the upper edge portion sides of the leg portions 136c and 136d. The pin hole insertion portions are coupled to each other by the pin receiving portion 128c of the distal end portion of the drive pipe 128 and the coupling pin 142. Therefore, the pin receiving portion 128c of the distal end portion of the drive pipe 128 and the proximal end portions of the arms 136a and 136b of the jaw main body 136 are coupled to each other by the coupling pin 142. When the drive pipe 128 proceeds or retreats along the axial direction of the jaw assembly 26 with respect to the jaw support member 132, the distal-end action portion 134 is rotated on the pivot studs 140a and 140b with respect to the distal end portion of the jaw support member 132.

The front-end action portion 134 is closed by causing the drive pipe 128 to proceed toward the distal end side. In the closing operation of the distal-end action portion 134, the grip member 138 of the distal-end action portion 134 is pressed against the treatment portion 46 of the vibration transmission member 40 of the probe 14, which allows the subject (biological tissue) to be gripped between the treatment portion 46 and the grip member 138 of the distal-end action portion 134. The distal-end action portion 134 is also used in the case where the biological tissue is peeled off.

Even if a part of the pin receiving portion 128c where strength is the weakest is broken in the distal end portion of the drive pipe 128, the jaw support member 132 and the drive pipe 128 are fixed and prevented from rotating by the engagement between the long holes 128a and the inward protrusion portions 132g and 132h. Therefore, in the assembly, the jaw support member 132 is also fixed to the sheath assembly 24 and prevented from the rotating, which prevents the disengagement between the outward protrusion portions 132i and 132j of the jaw support member 132 and the cam grooves 118a of the sheath assembly 24.

Thus, the jaw assembly 26 is configured (see FIG. 2A).

Figure 11A:
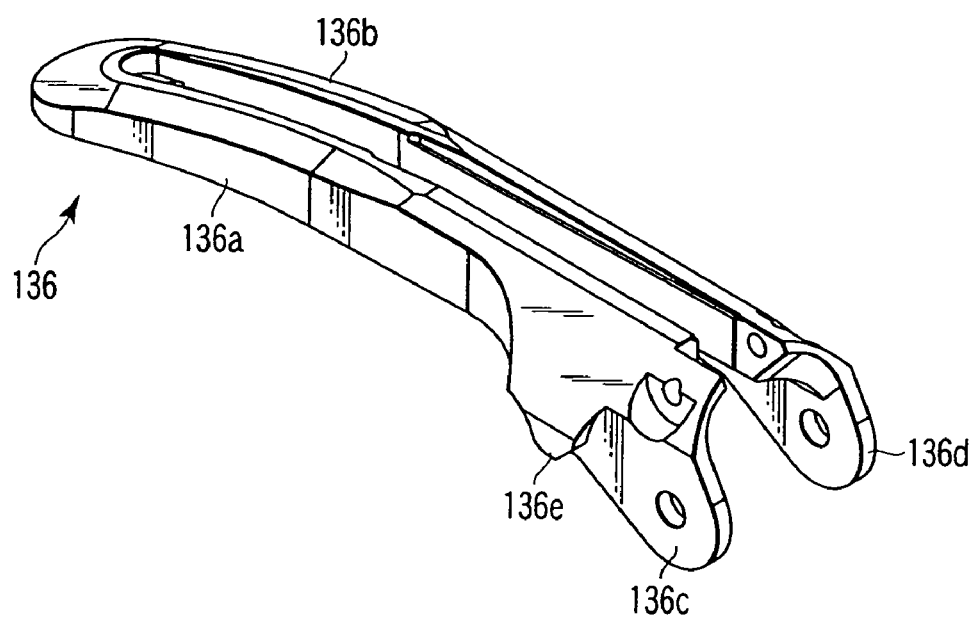
FIG. 11A is a schematic perspective view showing a jaw main body of a distal-end action portion in the jaw assembly of the main body unit assembly in the ultrasonic treatment instrument according to the first embodiment.
Figure 11B:
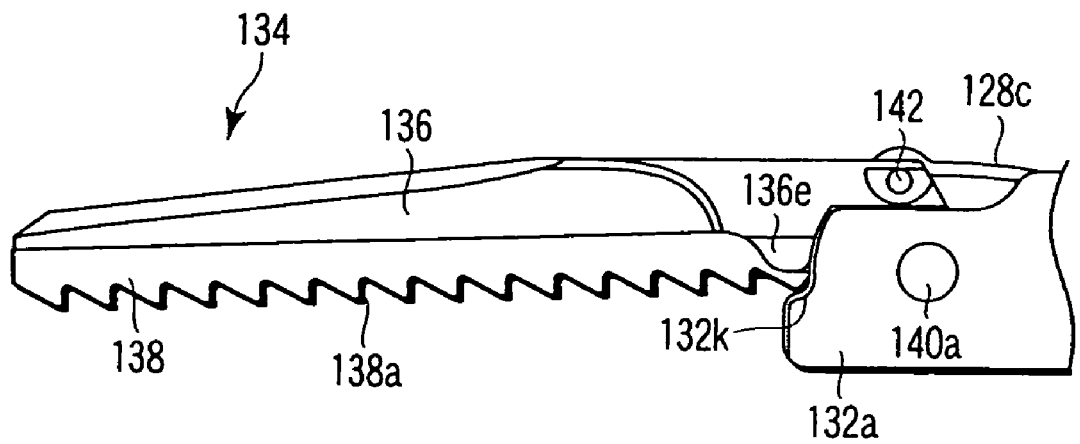
FIG. 11B is a schematic side view showing a state in which a projection portion of the jaw main body of the distal-end action portion in the jaw assembly is separated from a protrusion portion of a jaw support member in the ultrasonic treatment instrument according to the first embodiment.
Figure 11C:
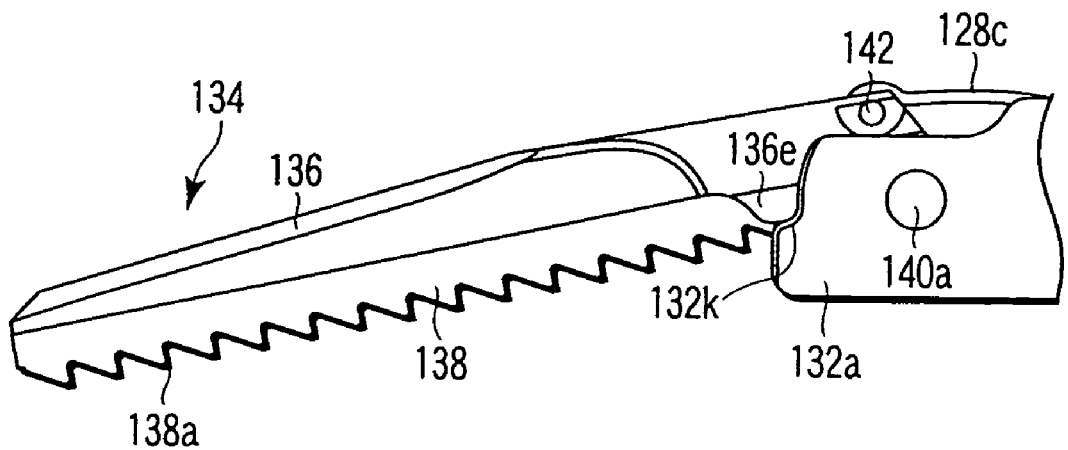
FIG. 11C is a schematic side view showing a state in which a projection portion of the jaw main body of the distal-end action portion in the jaw assembly is caused to abut on the protrusion portion of the jaw support member in the ultrasonic treatment instrument according to the first embodiment.

As shown in FIG. 11A, the proximal end surfaces of the proximal end portions of the arms 136a and 136b of the jaw main body 136 are formed in the arch shape as described above. Therefore, the strength in the proximal end portions of the arms 136a and 136b or the leg portions 136c and 136d is increased higher than, e.g., the substantially rectangular shape or the U-shape in the same thickness, which allows the proximal end portions of the arms 136a and 136b or the leg portions 136c and 136d to be formed in the thin manner while the same strength is maintained when compared with the substantially rectangular shape or the U-shape. Accordingly, the proximal end surface of the proximal end portion of the jaw main body 136 is formed smaller than the substantially rectangular shape or the U-shape while the same strength is maintained. Thus, the proximal end surface of the proximal end portion of the jaw main body 136 is formed smaller, and thereby the jaw main body 136 is formed smaller as a whole.

In the outer peripheral surfaces of the arms 136a and 136b of the jaw main body 136, projection portions 136e are formed at front positions of the leg portion 136c and 136d. The projection portions 136e are formed thicker than the leg portions 136c and 136d. As shown in FIG. 11B and 1C, protrusion portions 132k abutting on the projection portions 136e of the jaw main body 136 are formed in the arms 132a and 132b of the distal end portion of the jaw support member 132. Therefore, for example, as shown in FIG. 11C, the protrusion portion 132k of the jaw support member 132 can be received by the projection portion 136e which is thicker than the jaw main body 136, even if the projection portion 136e and the protrusion portion 132k abut on each other. Therefore, the application of the large force to the treatment portion 46 or the like is prevented, even if the jaw main body 136 is closed while no subject is sandwiched between the grip member 138 and the treatment portion 46 of the probe 14. That is, the stress applied to the treatment portion 46 by the ultrasonic vibration is restricted to delay fatigue fracture of the probe 14.

Next, the action of the ultrasonic treatment instrument 10 according to the first embodiment will be described.

As shown in FIG. 2, the ultrasonic treatment instrument 10 is separated into the main body unit assembly 12, the probe 14, and the vibrator assembly 16. The main body unit assembly 12 is separated into the handle assembly 22, the jaw assembly 26, and the sheath assembly 24.

In the case where the ultrasonic treatment instrument 10 is assembled, in this case, the insertion portion unit assembly 28 is first constructed by assembling the sheath assembly 24 and the jaw assembly 26 shown in FIG. 12.

Figure 13A:
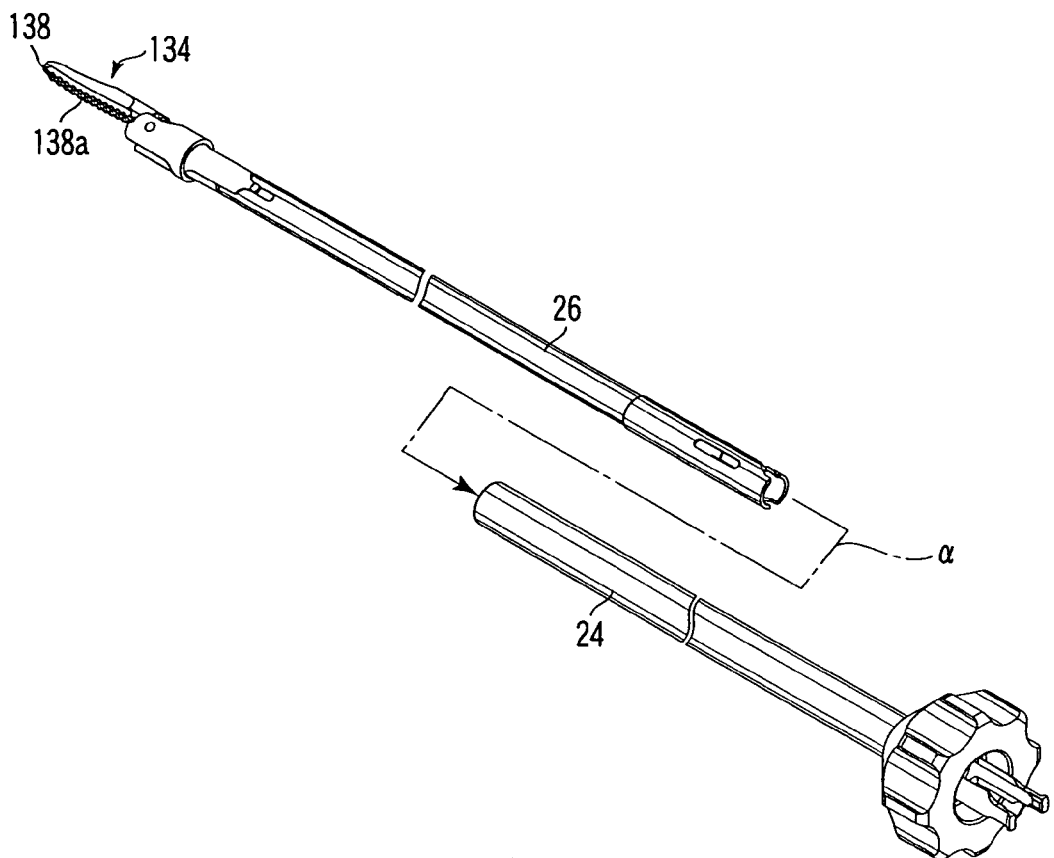
FIG. 13A shows a procedure of assembling the ultrasonic treatment instrument according to the first embodiment.

As shown by an arrow α in FIG. 13A, the jaw assembly 26 is inserted toward the proximal end portion from the distal end portion of the sheath assembly 24. The jaw assembly 26 is inserted into the sheath assembly 24 to the position where the jaw assembly 26 cannot be inserted any more. At this point, the outward protrusion portions 132i and 132j (see FIG. 10B) of the second arms 132c and 132d in the jaw support member 132 of the jaw assembly 26 are aligned with the opening edge portions of the cam grooves 118a (see FIG. 8) in the long pipe 118 of the sheath assembly 24. Thus, the jaw assembly 26 is positioned with respect to the sheath assembly 24.

The insertion of the jaw assembly 26 into the sheath assembly 24 is continued in this state. The proximal end edge portion of the jaw assembly connecting member 126 in the proximal end portion of the jaw assembly 26 abuts on the inward protrusion portions 114e and 114f (see FIG. 8) of the fixed arms 114a and 114b in the proximal end portion of the sheath assembly connecting member 114 of the proximal end portion of the sheath assembly 24. Since the inward protrusion portions 114e and 114f are formed in the proximal end portions of the pair of fixed arms 114a and 114b, the inward protrusion portions 114e and 114f are broadened as the fixed arms 114a and 114b are pressed and broadened with a predetermined force. That is, the inward protrusion portions 114e and 114f are broadened in the direction in which the inward protrusion portions 114e and 114f are separated from each other by the elastic deformation of the fixed arms 114a and 114b.

On the other hand, the outward protrusion portions 132*i* and 132*j* of the jaw support member 132 of the jaw assembly 26 are inserted to the position where the outward protrusion portions 132*i* and 132*j* abut on the proximal end portions of the cam grooves 118*a* in the long pipe 118 of the sheath assembly 24. At this point, the distal ends of the arms 132*c* and 132*d* which are of the step portion of the jaw support member 132 of the jaw assembly 26 abut on the distal end surface of the end cover 120 of the sheath assembly 24.

Figure 13B:
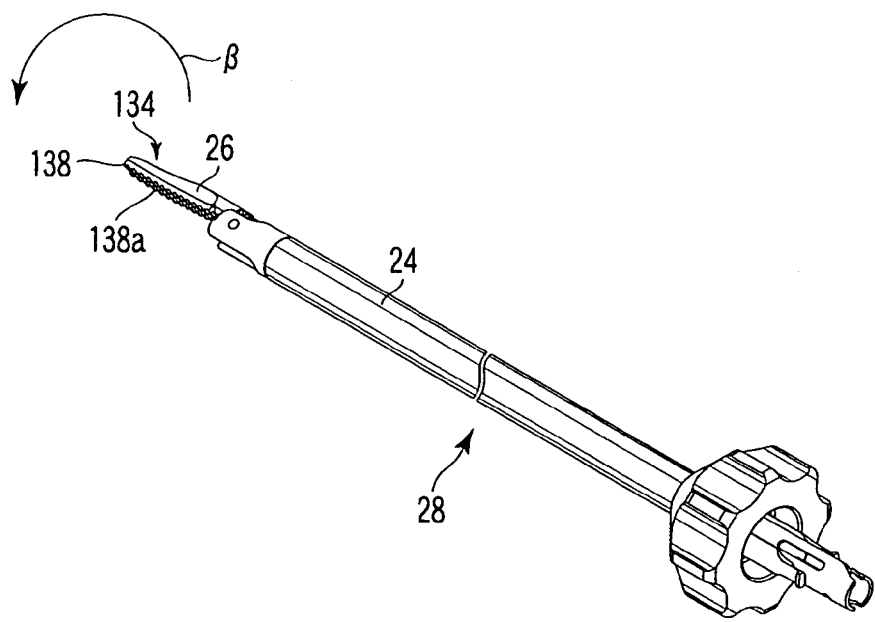
FIG. 13B shows a procedure of assembling the ultrasonic treatment instrument according to the first embodiment.

As shown by an arrow β in FIG. 13B, the grip surface 138*a* of the jaw assembly 26 is rotated downward from the front side with respect to the sheath assembly 24 while the grip surface (tooth portion) 138*a* of the grip member 138 is orientated toward the front side. That is, the sheath assembly 24 is rotated toward the rear side (clockwise) relative to the jaw assembly 26. In other words, the jaw assembly 26 is rotated toward the front side (counterclockwise) relative to the sheath assembly 24.

Then, the outward protrusion portions 132*i* and 132*j* of the jaw support member 132 of the jaw assembly 26 are rotated by about 60°, and the outward protrusion portions 132*i* and 132*j* abut on the deepest position of the L-shaped cam grooves 118*a* of the sheath assembly 24 to engage the cam grooves 118*a*.

At this point, the pair of inward protrusion portions 114*e* and 114*f* of the fixed arms 114*a* and 114*b* of the sheath assembly 24 are fitted from the outside into the pair of long holes 126*b* of the connecting member 126 in the proximal end portion of the jaw assembly 26 (see FIGS. 5 and 6A). That is, the elastic deformation of the fixed arms 114*a* and 114*b* is returned to the original state.

Figure 13C:
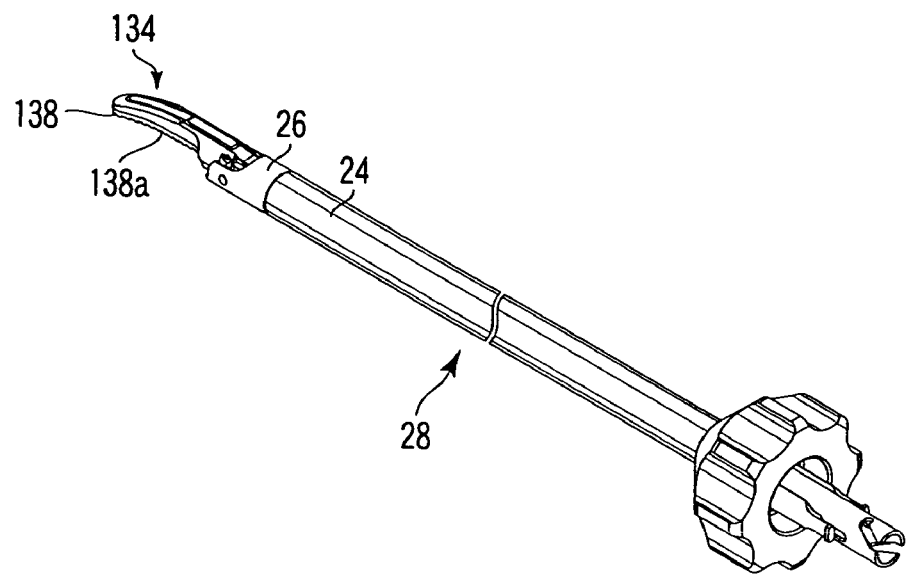
FIG. 13C shows a procedure of assembling the ultrasonic treatment instrument according to the first embodiment.

Accordingly, the jaw assembly 26 is assembled at two positions to the sheath assembly 24 to construct the insertion portion unit assembly 28 shown in FIG. 13C. In this state, the jaw assembly 26 is prevented from dropping off from the sheath assembly 24 except that the jaw assembly 26 is rotated counterclockwise with respect to the sheath assembly 24 by a force not lower than a constant force.

Then, the insertion portion unit assembly 28 in which the sheath assembly 24 and the jaw assembly 26 are integrated is assembled to the handle assembly 22. In this case, as shown by an arrow γ in FIG. 14A, the insertion portion unit assembly 28 is inserted through the inside of the distal end portion of the sheath connecting member 72 in the distal end portion of the handle assembly 22.

The fixed portions (outward projection portion) 114*c* and 114*d* of the connecting member 114 in the proximal end portion of the sheath assembly 24 are aligned with and inserted into the slits (enlarged holes) 72*a* and 72*b* of the sheath connecting member 72, shown in FIG. 6A, of handle assembly 22. Therefore, the insertion portion unit assembly 28 is positioned with respect to the handle assembly 22.

In the case where the fixed portions 114*c* and 114*d* of the connecting member 114 of the sheath assembly 24 are not aligned with the slits 72*a* and 72*b* of the sheath connecting member 72 of the handle assembly 22, the sheath assembly 24 cannot smoothly be inserted into the handle assembly 22.

In assembling the insertion portion unit assembly 28, after the jaw assembly 26 is inserted until the jaw assembly 26 abuts on the sheath assembly 24, sometimes the jaw assembly 26 is not rotated with respect to the sheath assembly 24, or sometimes the jaw assembly 26 is incompletely rotated with respect to the sheath assembly 24. In these cases, the inward protrusion portions 114*e* and 114*f* of the fixed arms 114*a* and 114*b* in the proximal end of the sheath assembly 24 are not fitted into the long holes 126*b* of the connecting member 126 in the proximal end portion of the jaw assembly 26, and the fixed arms 114*a* and 114*b* are left broadened in the direction in which the fixed arms 114*a* and 114*b* are separated from each other. Accordingly, the outer diameters of the fixed portions 114*c* and 114*d* becomes larger than the diameters of the slits 72*a* and 72*b* (see FIG. 6A) in the sheath connecting member 72, so that the fixed arms 114*a* and 114*b* cannot be inserted.

In the insertion portion unit assembly 28 positioned in the handle assembly 22, the fixed portions 114*c* and 114*d* of the sheath assembly connecting member 114 are caused to abut on the distal end portion of the rotating fixing member 68. In this state, the insertion portion unit assembly 28 is further inserted into the handle assembly 22. The rotating fixing member 68 is moved onto the proximal end portion side of the operation portion main body 54 against the biasing force of the coil spring 78, and the proximal end portion of the rotating fixing member 68 is caused to abut on the outer peripheral surface of the drive pipe connecting member 80.

Therefore, the drive pipe connecting pin 80*a* of the distal end portion of the drive pipe connecting member 80 is arranged in the opening portion at the rear end of the cam grooves 126*a* of the connecting member 126 in the proximal end portion of the jaw assembly 26. On the other hand, the fixed portions 114*c* and 114*d* of the sheath assembly connecting member 114 pass through the slits 72*a* and 72*b* in the sheath connecting member 72 onto the proximal end portion side, which allows the fixed portions 114*c* and 114*d* to be rotated about the axis. The slits 72*a* and 72*b* are used for the positioning in the rotation direction As shown by an arrow δ in FIG. 14B, the grip surface 138*a* of the insertion portion unit assembly 28 is rotated downward from the front side with respect to the handle assembly 22 while the grip surface 138*a* of the distal-end action portion 134 is orientated toward the front side. That is, the handle assembly 22 is rotated toward the rear side (clockwise) relative to the insertion portion unit assembly 28. In other words, the insertion portion unit assembly 28 is rotated toward the front side (counterclockwise) relative to the handle assembly 22.

Then, as shown in FIG. 6A, the rotating fixing member 68 is biased toward the distal end side by the coil spring 78 when the positions in the rotation direction about the axis of the fixed arms 114*a* and 114*b* match up with the slit portions 68*a* and 68*b* of the distal end portion of the rotating fixing member 68. The rotating fixing member 68 is returned to the position where the first pin 70*a* abuts on the distal end side of the slit 66*c* of the rotating hook member 66. The slit portions 68*a* and 68*b* of the rotating fixing member 68 engage the fixed portions 114*c* and 114*d* of the fixed arms 114*a* and 114*b* of the sheath assembly connecting member 114. Therefore, the sheath assembly 24 is fixed, and prevented from the rotating about the axis of the rotating fixing member 68. As shown in FIG. 5, at the same time, the drive pipe connecting pins 80*a* are drawn and inserted to the deep position by the cam grooves 126*a* of the proximal end portion of the connecting member 126 of the jaw assembly 26, and the drive pipe connecting pins 80*a* are fixed in the axial direction.

In the fixed portions (outward projection portions) 114*c* and 114*d* of the fixed arms 114*a* and 114*b* of the sheath assembly connecting member 114, because the positions in the rotation direction about the axis are shifted from the slits 72*a* and 72*b* of the sheath connecting member 72 (see FIG. 6A), the sheath assembly 24 is fixed in the axial direction (longitudinal direction) with respect to the handle assembly 22. In the outer peripheries of the fixed arms 114*a* and 114*b* of the sheath assembly connecting member 114, the deformation in the radially outward direction is suppressed by the hole portion inside the sheath connecting member 72 of the handle assembly 22. Therefore, in the state in which the insertion portion unit assembly 28 and the handle assembly 22 are assembled, the jaw assembly 26 is fixed to the sheath assembly 24 while the rotation of the jaw assembly 26 is completely prevented. Accordingly, the outward protrusion portions 132i and 132j of the jaw support member 132 never disengage the cam grooves 118a of the long pipe 118 of the sheath assembly 24, and the jaw support member 132 is completely fixed to the sheath assembly 24 in the axial direction. This enables the insertion portion unit assembly 28 to be fixed to the rotating fixing member 68 while the insertion portion unit assembly 28 and the rotating fixing member 68 are prevented from relatively rotating about the axis. Therefore, the rotating hook member 66 is fixed by the first pin 70a, the drive pipe connecting member 80 is fixed by the third pin 70c, and the rotating hook member 66 and the drive pipe connecting member 80 are prevented from rotating about the axis. Therefore, the drive pipe connecting pin 80a of the drive pipe connecting member 80 moves the rotating fixing member 68 toward the proximal end side, and the insertion portion unit assembly 28 and the drive pipe connecting member 80 are prevented from dropping off from the handle assembly 22 unless the insertion portion unit assembly 28 and the drive pipe connecting member 80 become rotatable.

Figure 14A:
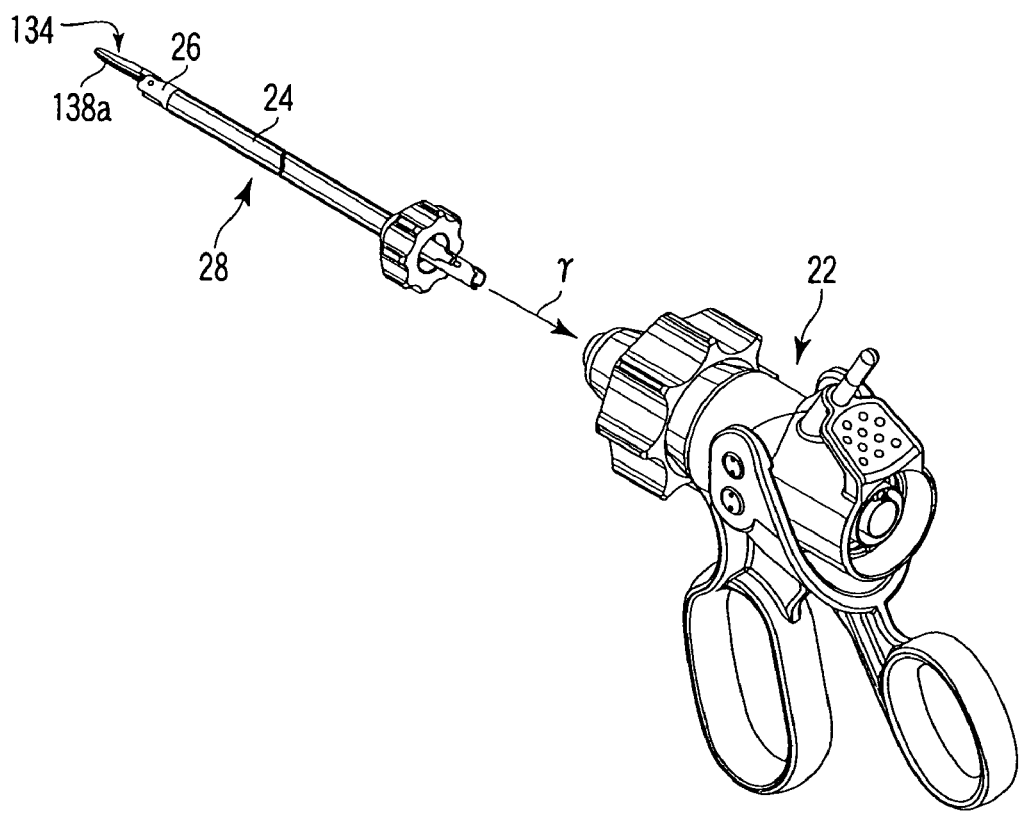
FIG. 14A shows a procedure of assembling the ultrasonic treatment instrument according to the first embodiment.
Figure 14B:
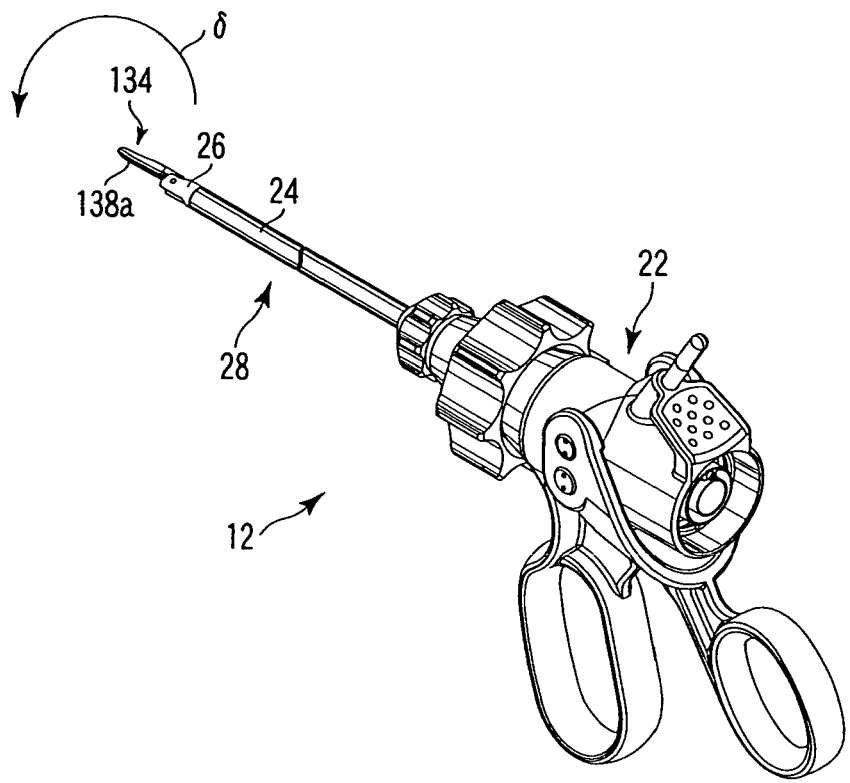
FIG. 14B shows a procedure of assembling the ultrasonic treatment instrument according to the first embodiment.
Figure 14C:
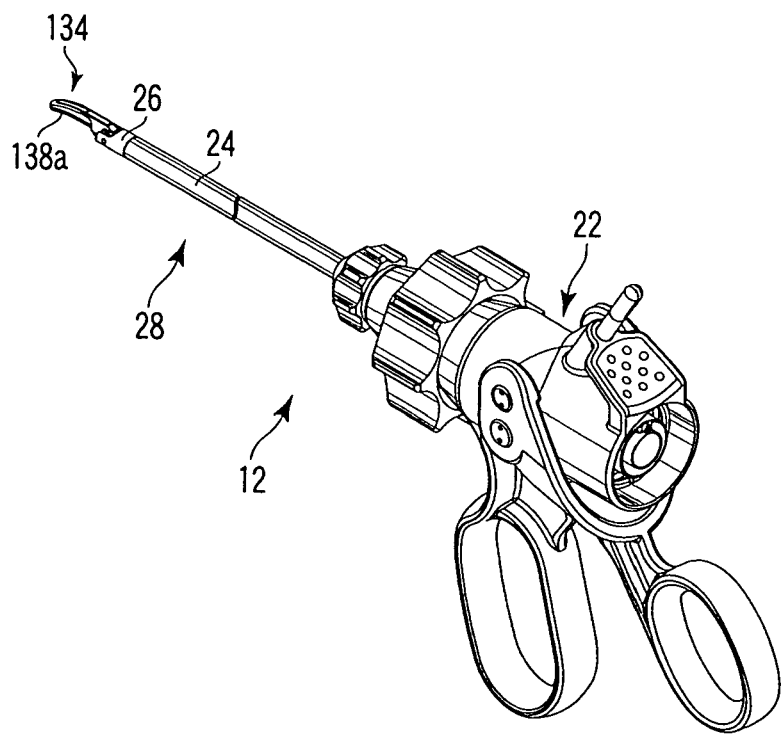
FIG. 14C shows a procedure of assembling the ultrasonic treatment instrument according to the first embodiment.

Accordingly, the insertion portion unit assembly 28 is assembled at two positions to the handle assembly 22 to construct the main body unit assembly 12 shown in FIG. 14C.

As shown in FIG. 2, the probe 14 and the vibrator assembly 16 are coupled to each other. In this case, the mounting screw 44a in the proximal end portion of the probe 14 is screwed into the thread hole portion of the probe attachment portion in the distal end portion of the horn of the vibrator assembly 16.

In this state of things, the probe 14 is inserted from the proximal end portion of the handle assembly 22 toward the distal end portion of the insertion portion unit assembly 28. In the insertion, the parallel plane 48a and 48b (see FIG. 2B) of the irregular sectional shape portion 48 of the probe 14 are positioned at predetermined positions by the parallel planes 90a and 90b of the positioning member 90 of the handle assembly 22. For example, in the first embodiment, the parallel plane 48a and 48b can symmetrically be inserted at two positions at the angle of 180°. However, an operator inserts the probe 14 in the direction in which the shape of the treatment portion 46 of the probe 14 coincides with the shape of the distal-end action portion 134 of the jaw assembly 26.

The probe 14 is inserted to the proximal end portion of the probe 14, and the assembly coupling portion 32 (see FIG. 2A) of the vibrator assembly 16 is mounted to the proximal end portion of the handle assembly 22. Therefore, the assembly coupling portion 32 of the vibrator assembly 16 engages the vibrator connecting portion 99 formed by the vibrator assembly guide 96 and C-ring receiving member 98 of the handle assembly 22. Accordingly, the treatment portion 46 of the probe 14 is protruded to the position facing the distal-end action portion 134, and the ultrasonic treatment instrument 10 is assembled (see FIG. 1).

The working of the ultrasonic treatment instrument 10 assembled in the above manner will be described below.

When the operator rotates the rotating knob 74, the rotating hook member 66 is rotated though the first pin 70a rotatably fixed to the rotating knob 74 by following the rotation of the rotating knob 74. When the rotating hook member 66 is rotated, the sheath connecting member 72 and the fixing member 76 are rotated. The sheath connecting member 72 and the fixing member 76 are fixed by the inner peripheral surface of the distal end portion of the rotating hook member 66.

Then, the drive pipe connecting member 80 coupled to the third pin 70c engaging the slit 66c of the rotating hook member 66 is rotated. When the drive pipe connecting member 80 is rotated, the slider receiving member 82 coupled by the second pin 70b is rotated. When the slider receiving member 82 is rotated, the positioning member 90 coupled by the fourth pin 70d is rotated, which rotates the rotating fixing member 68 coupled to the first pin 70a, the sheath assembly connecting member 114 of the sheath assembly 24 engaged by the slit portions 68a and 68b of the rotating fixing member 68, and the jaw assembly connecting member 126 of the jaw assembly 26 engaged by the inward protrusion portions 114e and 114f of the sheath assembly connecting member 114. Further, other members integrally fixed to these members are rotated by following the rotations of these members. That is, the rotating fixing member 68, the rotating hook member 66, the sheath connecting member 72, the drive pipe connecting member 80, the slider receiving member 82, the positioning member 90, the contact pipe 92, and the vibrator assembly guide 96 are rotated relative to the operation portion main body 54, when the operator rotates the rotating knob 74. Therefore, when the rotating knob 74 is rotated, the sheath assembly 24 and the jaw assembly 26 are also rotated according to the rotation of the rotating knob 74.

Then, the operator holds the finger through-holes 56a and 58a of the fixed handle 56 and movable handle 58 to rotate the movable handle 58 with respect to the fixed handle 56. The finger through-hole 58a of the movable handle 58 is brought close to the finger through-hole 56a of the fixed handle 56. That is, the fixed handle 56 and the movable handle 58 are relatively closed.

The movable handle 58 is rotated on the fulcrum pin 60 of the operation portion main body 54. The action pin 62 is moved in the arc on the fulcrum pin 60 in connection with the working of the movable handle 58. The end portion of the action pin 62 is engaged by the pin receiving portion 86a of the slider 86 in the operation portion main body 54. Therefore, the slider 86 is pushed out toward the distal end side in the axial direction to convert the force for closing the movable handle 58 into the force on the distal end side in the axial direction. On the contrary, when the operation for opening the movable handle 58 is performed, the slider 86 is pushed out toward the rear end side in the axial direction to convert the force for opening the movable handle 58 into the force on the rear end side in the axial direction.

The slider 86 is biased to the slider receiving member 82 with a constant force toward the rear end side in the axial direction by the driving force restriction spring 88. Therefore, in the case where the force generated on the distal end side in the axial direction by the closing operation of the movable handle 58 is not more than the capacity of the driving force restriction spring 88, the slider 86 slides toward the distal end direction while being integral with the slider receiving member 82 and the drive pipe connecting member 80. In the case where the force generated on the distal end side in the axial direction by the closing operation of the movable handle 58 is more than the capacity of the driving force restriction spring 88, the slider 86 slides toward the distal end side in the axial direction against the driving force restriction spring 88 with respect to the slider receiving member 82 and the drive pipe connecting member 80. Therefore, transmission of the axial force on the distal end side in the axial direction not lower than the predetermined force to the drive pipe connecting member 80 is prevented.

In the case where the force generated on the distal end side in the axial direction by the closing operation of the movable handle 58 is not more than the capacity of the driving force restriction spring 88, as described above, the drive pipe connecting member 80 also slides integrally toward the distal end side. The force generated on the distal end side in the axial direction is transmitted to the jaw assembly connecting member 126 though the drive pipe connecting pin 80*a*. The jaw assembly connecting member 126 is located in the proximal end portion jaw assembly 26, and the jaw assembly connecting member 126 engages the drive pipe connecting pin 80*a*. The jaw support member 132 is fixed in the axial direction by the engagement with the sheath assembly 24. Therefore, the drive pipe 128 coupled to the jaw assembly connecting member 126 slides in the distal end direction with respect to the jaw support member 132. The drive pipe 128 is coupled to the jaw main body 136 by the pin receiving portion 128*c* of the distal end portion. The jaw main body 136 is rotatably attached by the jaw support member 132 and the pivot studs 140*a* and 140*b*, which rotates the jaw main body 136 downward on the fulcrums of the pivot studs 140*a* and 140*b* (see FIG. 11C).

Accordingly, the biological tissue is sandwiched between the grip surface 138*a* of the grip member 138 of the distal-end action portion 134 and the treatment portion 46 of the probe 14 to close the movable handle 58, which allows the biological tissue to be gripped. On the contrary, in the case where the movable handle 58 is operated in the direction in which the movable handle 58 is opened with respect to the fixed handle 56, the jaw main body 136 is rotated upward on the fulcrums of the pivot studs 140*a* and 140*b* by the reverse action of the above-described action, which enables the operation in which the jaw main body 136 and the grip member 138 are opened.

When the ultrasonic vibrator of the vibrator assembly 16 is vibrated while the biological tissue is gripped, the ultrasonic vibration is transmitted to the treatment portion 46 from the maximum diameter portion 44 of the probe 14 through the horn portion 42 and the vibration transmission member 40. The biological tissue receives the force in the closing direction with respect to the treatment portion 46 of the probe 14 from the grip surface 138*a* of the grip member 138 through the jaw main body 136. In this state, when the ultrasonic vibration is transmitted, frictional heat is generated in the surface where the biological tissue is in contact with the treatment portion 46, which generates the solidifying action. The biological tissue which becomes brittle by the solidifying action is mechanically cut by the ultrasonic vibration. Thus, the treatment such as the solidifying or the cutting is performed.

A cord for supplying high-frequency current from a high-frequency power source is connected to a high-frequency connecting pin 94, and the high-frequency current is supplied from the high-frequency power source. Therefore, the high-frequency current is passed through the probe 14 from the irregular sectional shape portion 48 of the probe 14 through the high-frequency connecting pin 94, the vibrator assembly guide 96, the connector 92*a*, the contact pipe 92, and the positioning member 90. Therefore, the high frequency current is transmitting to the treatment portion 46 through the irregular sectional shape portion 48, the horn portion 42, and the vibration transmission member 40. Accordingly, while the biological tissue is gripped, or while the treatment portion 46 is brought into contact with the biological tissue, when the high-frequency current is supplied between the grip surface 138*a* of the grip member 138 of the distal-end action portion 134 and the treatment portion 46 of the probe 14 facing the grip surface 138*a*, the high-frequency treatment is performed on the biological tissue by Joule heat using the treatment portion 46.

Even if a part of the pin receiving portion 128*c* where the strength is the weakest is broken in the drive pipe 128 of the jaw assembly 26, the inward protrusion portions 132*g* and 132*h* of the jaw support member 132 are engaged in the long holes 128*a* of the drive pipe 128 while the inward protrusion portions 132*g* and 132*h* and the long hole 128*a* are fixed in the rotation direction, so that the jaw support member 132 is fixed to the sheath assembly 24 through the drive pipe 128 and the jaw assembly connecting member 126 while the rotation of the jaw support member 132 is prevented. Accordingly, the engagement is never released between the outward protrusion portions 132*i* and 132*j* of the jaw support member 132 and the cam grooves 118*a* in the distal end portion of the long pipe 118 of the sheath assembly 24, which prevents the distal end portion from dropping off from the jaw support member 132.

After the ultrasonic treatment or the high-frequency treatment is finished, the ultrasonic treatment instrument 10 is disassembled in order to clean the assemblies 14, 16, 22, 24, and 26. In this case, first the probe 14 and the vibrator assembly 16 are detached from the handle assembly 22 by the reverse action of the above-described action.

Figure 15A:
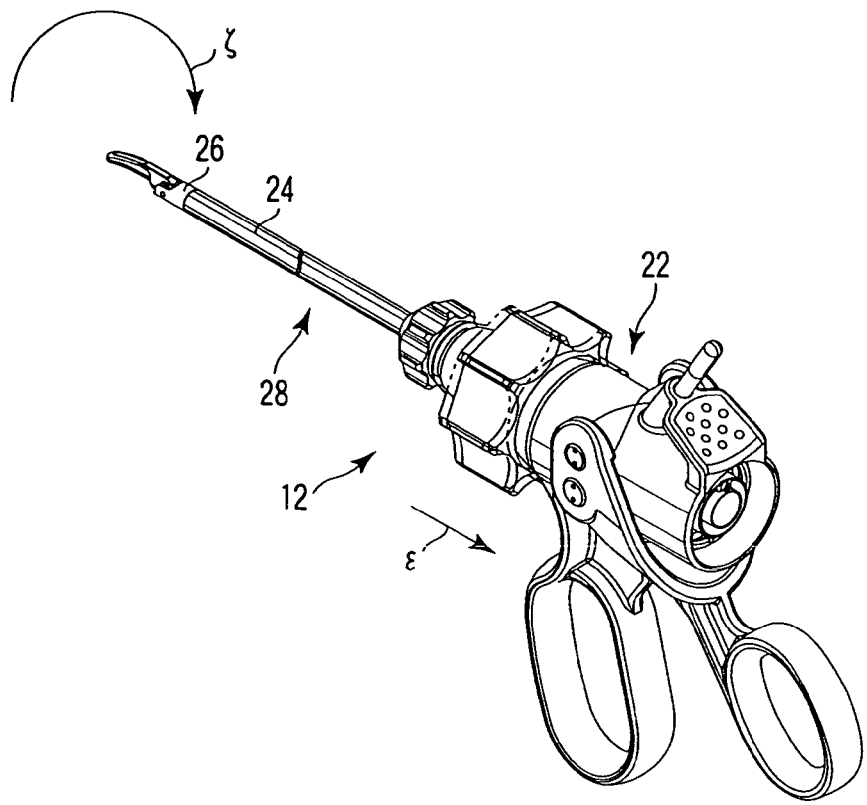
FIG. 15A shows a procedure of disassembling the ultrasonic treatment instrument according to the first embodiment.
Figure 15B:
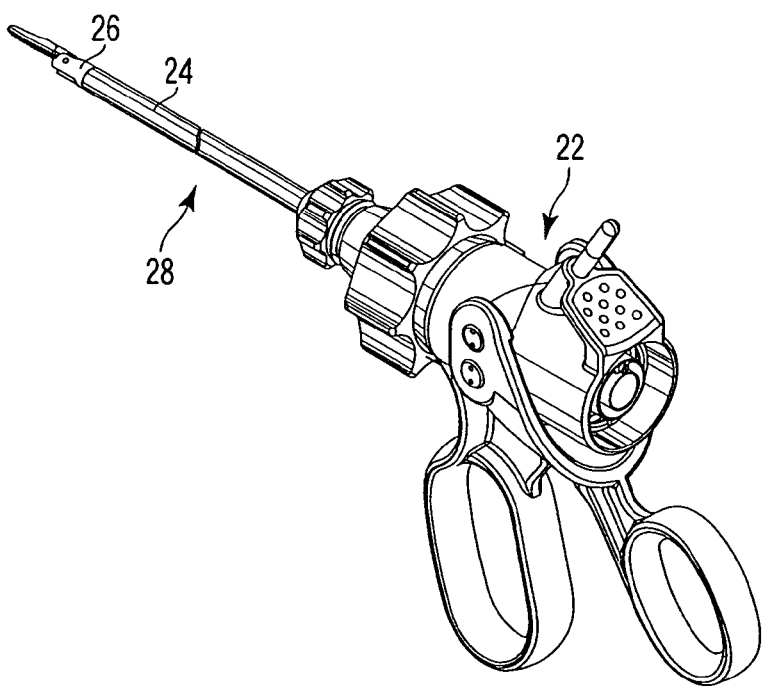
FIG. 15B shows a procedure of disassembling the ultrasonic treatment instrument according to the first embodiment.
Figure 15C:
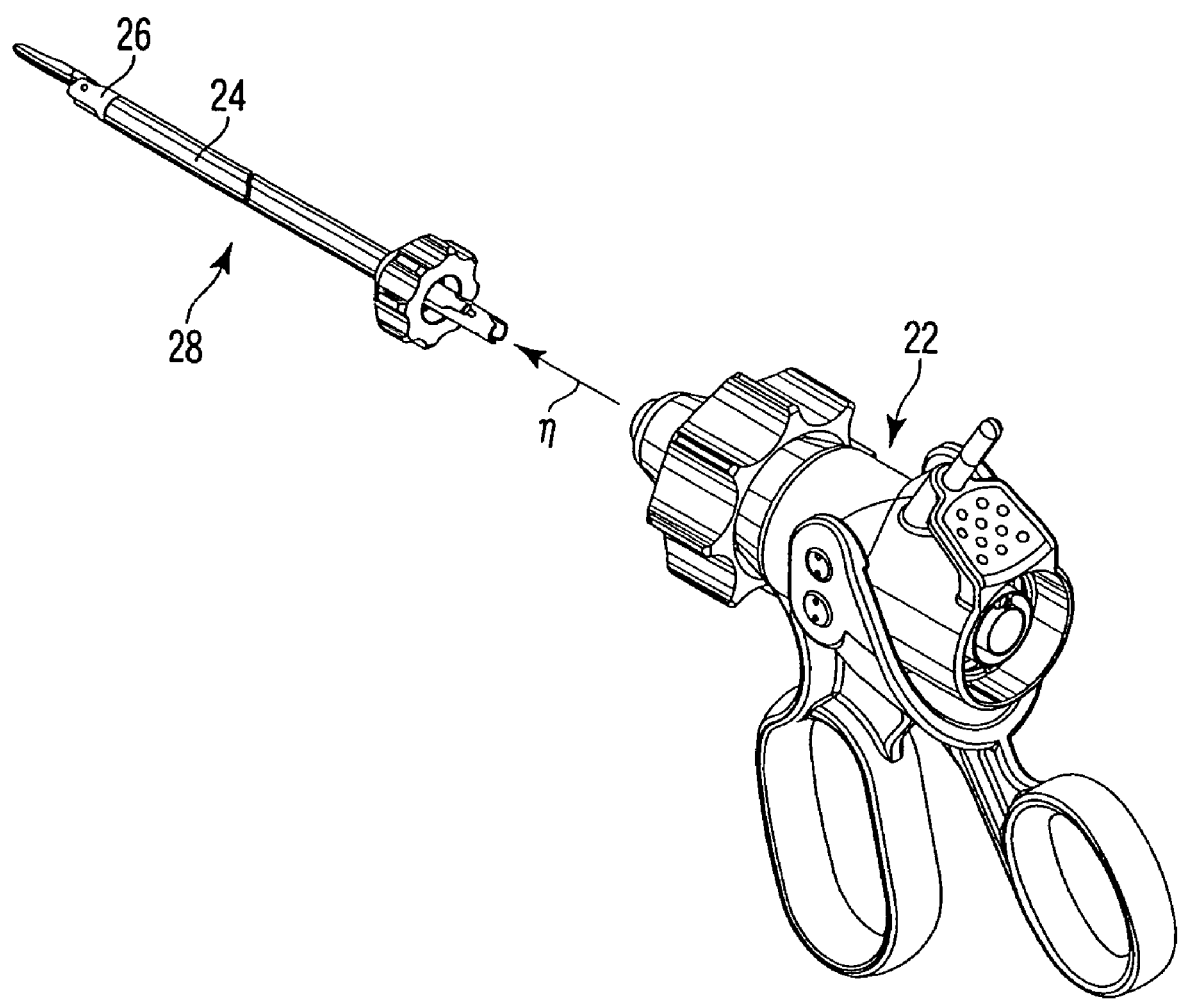
FIG. 15C shows a procedure of disassembling the ultrasonic treatment instrument according to the first embodiment.

As shown by an arrow ε in FIG. 15A, the rotating knob (unlocking mechanism) 74 of the handle assembly 22 is drawn onto the proximal end portion side of the operation portion main body 54. Since the rear end surface of the rotating knob 74 abuts on the head portion of the first pin 70*a*, the rotating fixing member 68 is moved toward the proximal end portion side of the operation portion main body 54 while compressing the coil spring 78 toward the side of the flange portion 66*b* of the rotating hook member 66. At this point, the engagement is released between the slit portions 68*a* and 68*b* (see FIG. 6A) in the distal end portion of the rotating fixing member 68 and the fixed portions 114*c* and 114*d* of the fixed arms 114*a* and 114*b*. That is, the engagement is released between the rotating fixing member 68 and the sheath assembly connecting member 114, which allows the insertion portion unit assembly 28 to be rotated with respect to the sheath connecting member 72.

In this state, the knob 112 of the sheath assembly 24 is gripped to rotate the insertion portion unit assembly 28, in which the sheath assembly 24 and the jaw assembly 26 are integrated, by about 60° in the opposite direction to the way in which the ultrasonic treatment instrument 10 is assembled. That is, the insertion portion unit assembly 28 is rotated as shown by an arrow ζ in FIG. 15A. Therefore, the fixed portions (outward protrusion portion) 114*c* and 114*d* of the sheath assembly connecting member 114 are aligned with the positions of the slits 72*a* and 72*b* of the sheath connecting member 72.

At the same time, the drive pipe connecting pins 80*a* of the drive pipe connecting member 80 are arranged in the opening portions of the cam grooves 126*a* in the proximal end of the jaw assembly connecting member 126 to release the engagement in the axial direction. In this state of things, as shown by an arrow η in FIG. 15C, the insertion portion unit assembly 28 is detached from the sheath connecting member 72.

Then, the insertion portion unit assembly 28 is disassembled into the sheath assembly 24 and the jaw assembly 26. In this case, the reverse operation of the way in which the sheath assembly 24 and the jaw assembly 26 are assembled is performed. Therefore, the insertion portion unit assembly 28 is disassembled into the sheath assembly 24 and the jaw assembly 26.

Then, the probe 14 and the vibrator assembly 16 are disassembled. For this purpose, the way in which the ultrasonic treatment instrument 10 is disassembled into the five assemblies of the probe 14, the vibrator assembly 16, the handle assembly 22, the sheath assembly 24, and the jaw assembly 26 is ended.

In this state of things, the assemblies 14, 16, 22, 24, and 26 are cleaned and disinfected so as to be reusable. In the case of the reuse, the ultrasonic treatment instrument 10 is assembled in the above-described manner.

As described above, the following effects are obtained in the first embodiment.

For example, even in the case where a part of any one of the handle assembly 22, the sheath assembly 24, and the jaw assembly 26 is worn or broken, the ultrasonic treatment instrument 10 can be used again merely by replacing the worn or broken assembly and assembling it, so that the cost associated with the replacement can be reduced.

In the main body unit assembly 12, the sheath assembly 24 and the jaw assembly 26 can be detached from the handle assembly 22. Therefore, the assemblies 22, 24, and 26 can securely be cleaned in a short time without using any special cleaning tool. Accordingly, the cleaning cost of the main body unit assembly 12 can be reduced.

In the drive pipe 128 of the jaw assembly 26 where a large force is applied in the use of the ultrasonic treatment instrument 10, even if the pin receiving portion 128c of the distal end portion where the strength is the weakest is broken, the jaw support member 132 is fixed to the drive pipe 128 while the rotations of the jaw support member 132 and drive pipe 128 are prevented. Therefore, the engagement with the cam groove 118a in the distal end portion of the long pipe 118 of the sheath assembly 24 is never released, which prevents the distal end portion from dropping off from the jaw support member 132.

The action, in which the insertion portion unit assembly 28 is mounted to the handle assembly 22 to assemble the main body unit assembly 12 after the insertion portion unit assembly 28 is constructed, is described in the first embodiment. Alternatively, for example, the structure in which the jaw assembly 26 is mounted to the sheath assembly 24 and handle assembly 22 to assemble the main body unit assembly 12 after the sheath assembly 24 is amounted to the handle assembly 22 may be adopted.

The action in which the insertion portion unit assembly 28 is disassembled into the two assemblies 24 and 26 after the insertion portion unit assembly 28 is disassembled from the handle assembly 22 is described in the case where the main body unit assembly 12 is disassembled into the three assemblies 22, 24, and 26. Alternatively, for example, the structure in which the sheath assembly 24 is disassembled from the handle assembly 22 after the jaw assembly 26 is disassembled from the handle assembly 22 may be adopted.

Then, a second embodiment will be described with reference to FIGS. 16A to 18B. The second embodiment is a modification of the first embodiment, so that the same member as that described in the first embodiment is designated by the same numeral, and the detailed description will be omitted.

Figure 16A:
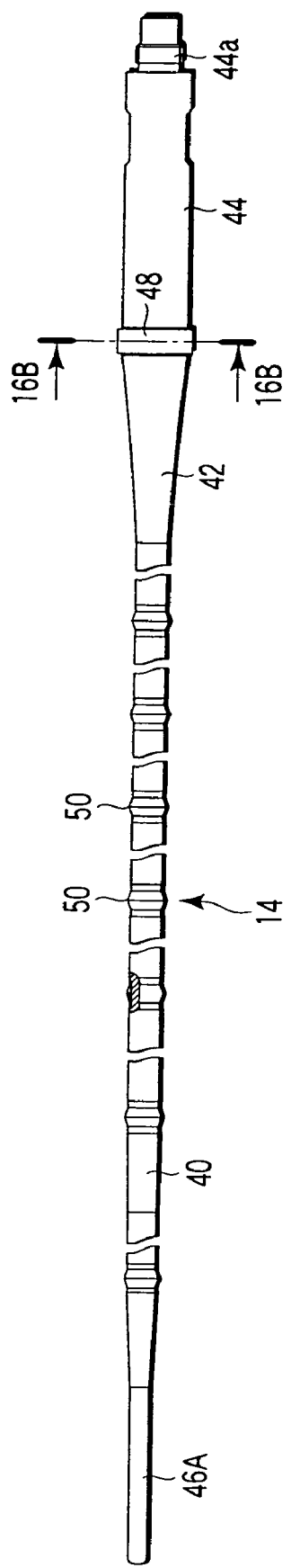
FIG. 16A is a schematic side view of a probe in an ultrasonic treatment instrument according to a second embodiment.
Figure 17:
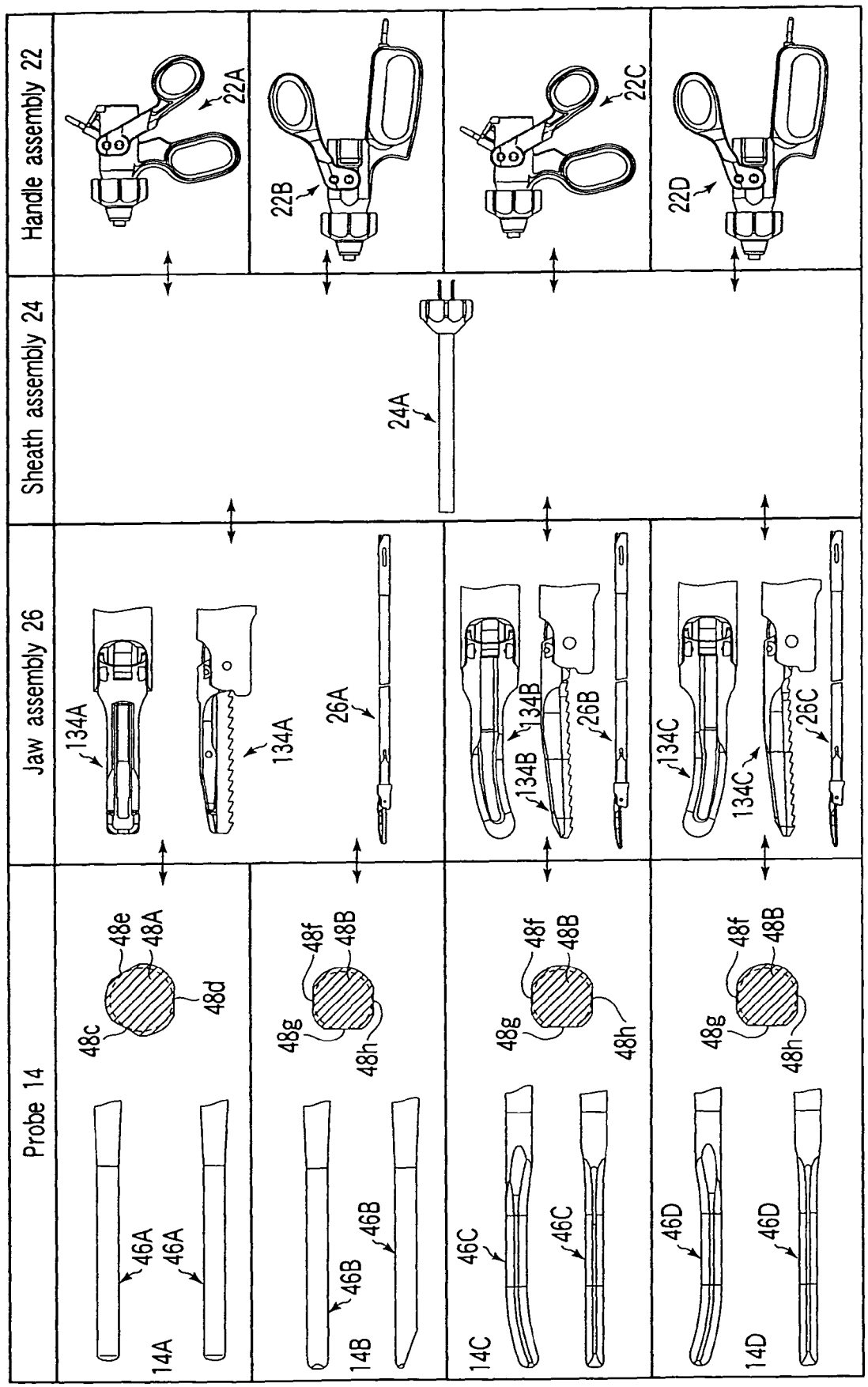
FIG. 17 is a schematic view showing an example of each lineup of probes, jaw assemblies, sheath assemblies, and handle assemblies in the ultrasonic treatment instrument according to the second embodiment.

In the second embodiment, for example, the probe 14 in which the treatment portion 46 (see FIG. 2A) is curved as described in the first embodiment is not used, but a treatment portion 46A formed in a straight line is used as shown in FIG. 16A. In the case of the different shape of the treatment portion 46 at the distal end of the probe 14, the probes 14 should differ from one another in the length when the probes 14 are designed such that the resonance frequencies of the probes 14 become equal to one another. The handle assembly 22 in which the assembling positions between the vibrator assembly 16 and the handle assembly 22 is shifted is required in order to be able to use the common sheath assembly 24. Therefore, as shown in FIG. 17, lining up of the various handle assemblies 22 and jaw assemblies 26 are required according to the probes 14 to be used. FIG. 17 shows an example of the line up.

Sections of the probe 14 in FIG. 17 illustrate four types of treatment portions 46 and the irregular sectional shape portion 48 corresponding to each treatment portion 46. A straight type 46A, a modified straight type 46B which is different from the straight type 46A in the distal end portion, and curved types 46C and 46D which are curved in the directions different from each other are sequentially shown in the treatment portion 46. An upper side of each section is a top view and a lower side is a side view. An irregular sectional shape portion 48A of the straight type treatment portion 46A is similar to that shown in FIG. 16B. The irregular sectional shape portion 48A (not shown) of the straight type treatment portion 46A may be similar to that shown in FIG. 2B. As described later, irregular sectional shape portions 48B of the modified straight type and curved type treatment portions 46B, 46C, and 46D include three flat portions 48f, 48g, and 48h and one curved surface portion.

The sections of the jaw assembly 26 illustrate three types. The uppermost section illustrates a straight type distal-end action portion 134A and a jaw assembly 26A having the straight type distal-end action portion 134A. In the straight type distal-end action portion 134A, the treatment portion 46 of the probe 14 is suitable to the probes 14A and 14B having the straight type 46A and the modified straight type 46B. The intermediate section illustrates a curved type distal-end action portion 134B and a jaw assembly 26B having the curved type distal-end action portion 134B. In the curved type distal-end action portion 134B, the treatment portion 46 of the probe 14 shown in the left side of FIG. 17 is suitable to the probe 14C having the curved type 46B. The lower section illustrates a curved type distal-end action portion 134C and a jaw assembly 26C having the curved type distal-end action portion 134C. In the curved type distal-end action portion 134C, the treatment portion 46 of the probe 14 shown in the left side of FIG. 17 is suitable for the probe 14D having the curved type 46C. An upper stage of each section is a top view of the distal-end action portion 134, an intermediate stage is a side view of the distal-end action portion 134, and a lower stage is a side view of the jaw assembly 26.

The sections of the handle assembly 22 illustrate four types. A handle assembly 22A in the uppermost section is seemingly similar to a handle assembly 22C of the third section. However, for example, the handle assembly 22A differs from the handle assembly 22C in inside configurations such as the positioning member 90 and the drive pipe connecting member 80. Similarly, a handle assembly 22B in the second section is seemingly similar to a handle assembly 22D of the lowermost section. However, the handle assembly 22B differs from the handle assembly 22D in the inside configurations. In the handle assemblies 22B and 22D, the movable handle 58 is arranged in the upper side of FIG. 17 with respect to the central axis of the operation portion main body 54.

The handle assembly 22 has a false attachment preventing mechanism which prevents the construction of the assemblies of false combination in the lineup. The false attachment preventing mechanism will be illustrated below.

As described above, the probes 14 differ from one another in the length by several millimeters in the axial direction, and this is to ensure they mate the different shapes of the treatment portion 46 located at the distal end of the probe 14 both physically, and in terms of resonant frequency. Therefore, for the treatment portion 46 of the probe 14 shown in FIG. 17, the straight type 46A differs from the modified straight type 46B in the length. The lengths of the curved types 46C and 46D become equal when degrees of curvature are equal in the curved types 46C and 46D. When the straight type 46A and modified straight type 46B are compared to the curved types 46C and 46D, the straight type 46A and modified straight type 46B differ from the curved types 46C and 46D in the length.

The length of the distal-end action portion 134 of the jaw assembly 26 and the abutting position between the handle assembly 22 and the vibrator assembly 16 are adjusted in order to enable the probes 14A, 14B, 14C, and 14D having different lengths to be used in one kind of sheath assembly 24. For example, the same distal-end action portion 134 of the jaw assembly 26 can be used in the probe 14 of the second embodiment including the treatment portions of the straight type 46A and modified straight type 46B.

On the other hand, since the probes 14 differ from one another in the length, it is necessary to replace the abutting position of the vibrator assembly 16 with the handle assembly 22 in order to combine the jaw assembly 26 and sheath assembly 24 having the same length. For example, in the second embodiment, one of the handle assemblies 22A and 22B is required for the probe 14A, and one of the handle assemblies 22C and 22D is required for the probes 14B, 14C, and 14D. In the jaw assemblies 26 corresponding to the lengths of the probes 14 having the treatment portions 46 of the modified straight type 46B and the curved types 46C and 46D, the distal-end action portions 134A, 134B, and 134C of the jaw assemblies 26A, 26B, and 26C differ from one another only in the length. Therefore, the abutting position (mounted position) between the handle assemblies 22C and 22D and the vibrator assembly 16 becomes similar. Accordingly, the handle assemblies 22C and 22D can be used for the jaw assemblies 26A, 26B, and 26C, and the handle assemblies 22C and 22D can be used for the probes 14B, 14C, and 14D.

Figure 16B:
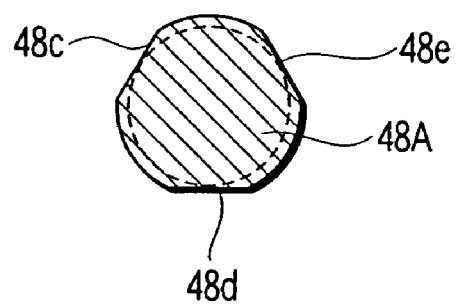
FIG. 16B is a sectional view taken on line 16B-16B in FIG. 16A of the probe in the ultrasonic treatment instrument according to the second embodiment.

The probe 14A shown in FIG. 16A includes the straight type cylindrical treatment portion 46A shown in FIG. 17. In this case, because the treatment portion 46A has a cylindrical shape, the treatment portion 46A functions even if the treatment portion 46A abuts on any position about the axis of the grip member 138 located in the distal-end action portion 134A of the jaw assembly 26A. Therefore, as shown in FIG. 16B, the three flat portions 48c, 48d, and 48e are provided in the outer peripheral surface of the irregular sectional shape portion 48A while a circumference is equally divided into three. That is, the flat portions 48c, 48d, and 48e are symmetrically formed with respect to the center of the irregular sectional shape portion 48A.

Positioning members (first attaching-and-detaching mechanism) (not shown) are formed in the handle assemblies 22A and 22B to which the probe 14A is mounted. The positioning member has a hole portion having the same shape as the irregular sectional shape portion 48A. Therefore, the probe 14A can be mounted at each 60° about the axis to the positioning members of handle assemblies 22A and 22B.

It is necessary that the treatment portions 46B, 46C, and 46D of the probes 14B, 14C, and 14D shown in FIG. 17 be positioned so as to abut on the distal-end action portions 134A, 134B, and 134C of the jaw assemblies 26A, 26B, and 26C only in one way respectively. Therefore, as shown in FIG. 17, the flat portions 48f, 48g, and 48h are provided at 90° apart three points in the outer peripheral surface of the irregular sectional shape portion 48B. It is preferable that the surface which connects the flat portions 48f and 48h be formed by, for example the curved surface or the plural flat surfaces except for one flat surface.

The positioning members (first attaching-and-detaching mechanism) (not shown) are formed in the handle assemblies 22C and 22D to which the probes 14B, 14C, and 14D are mounted. The positioning member has a hole portion having the same shape as the irregular sectional shape portion 48B. Therefore, the probes 14B, 14C, and 14D can be assembled only in one way to the positioning member, the slider receiving member 82, and the drive pipe connecting member 80 of the handle assemblies 22C and 22D.

Figure 18A:
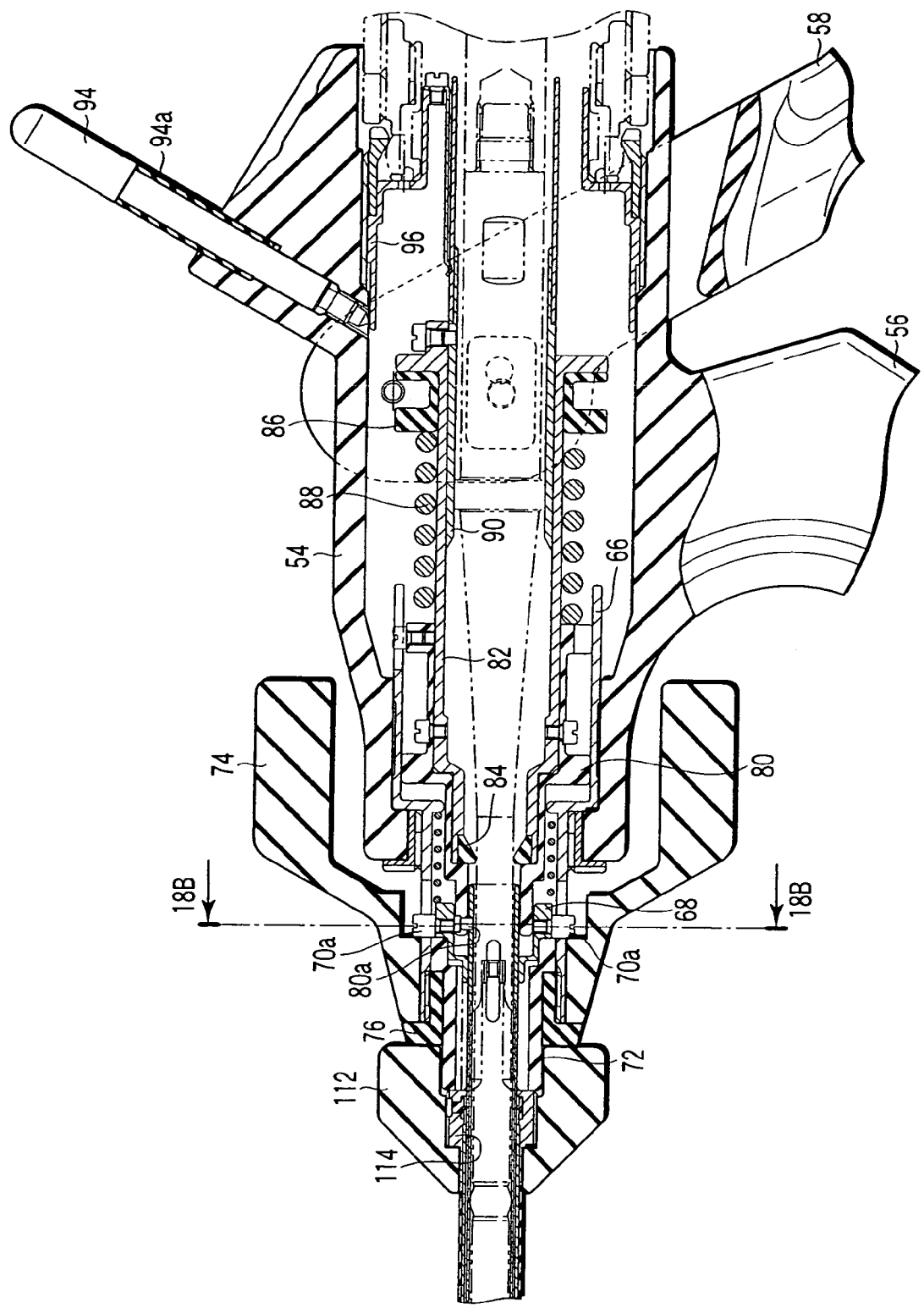
FIG. 18A is a longitudinal sectional view of the handle assembly of the main body unit assembly in the ultrasonic treatment instrument according to the second embodiment.

In the second embodiment, as shown in FIGS. 18A and 18B, only one drive pipe connecting pin (second attaching-and-detaching mechanism) 80a is arranged at the distal end of the drive pipe connecting member 80 of each of the handle assemblies 22A, 22B, 22C, and 22D. Only one cam groove 126a engaging one drive pipe connecting pin 80a is provided in the jaw assembly connecting member 126 of each of the jaw assemblies 26A, 26B, and 26C. The insertion portion unit assembly 28 in which the jaw assembly 26 and sheath assembly 24 are assembled in the above configuration is positioned so as to be assembled only at one point to the positioning member 80, the slider receiving member 82, and the positioning member 90 of the handle assembly 22.

Therefore, as shown in FIG. 17, the irregular sectional shape portion 48A of the probe 14A differs from the irregular sectional shape portions 48B of the probes 14B, 14C, and 14D in the shape. Accordingly, the probe 14A cannot be assembled to the handle assemblies 22C and 22D, and the probes 14B, 14C, and 14D cannot be assembled to the handle assemblies 22A and 22B.

In the case where the false combination of the probes 14A, 14B, 14C, and 14D and the jaw assemblies 26A, 26B, and 26C is completely prevented, at least two drive pipe connecting pins 80a in the handle assembly are produced at different positions such that each of the jaw assemblies 26A, 26B, and 26C is assembled only at one point to the corresponding handle assembly 22 (see FIGS. 5 and 6B). On the other hand, the cam grooves 126a in which the number and the positions coincide with those of the drive pipe connecting pin 80a are arranged in the jaw assembly connecting member 126 on the sides of the jaw assemblies 26A, 26B, and 26C so as to engage the drive pipe connecting pin 80a. Therefore, each of the jaw assemblies 26A, 26B, and 26C can be assembled only at one point to the corresponding handle assembly 22.

As described above, the following effect is obtained in the second embodiment.

Through use of the false attachment preventing mechanism, incorrect attachment of various assemblies can be prevented.

The embodiments are specifically described with reference to the drawings. However, the invention is not limited to the above embodiments, but the invention includes all the modifications and changes which are made without departing from the scope of the invention.

The invention provides the ultrasonic treatment apparatus and the method of assembling and disassembling the main body unit assembly of the ultrasonic treatment apparatus. In the ultrasonic treatment apparatus according to the invention, the main body unit assembly can further be disassembled into the plural assemblies, which allows the main body unit assembly to be easily cleaned without using the dedicated cleaning adaptor or the like. Further, even if the grip member of the main body unit assembly is worn, or even if the component is broken, the main body unit assembly can be reused at low cost simply by replacing the assembly in which the grip member is worn or the component is broken.

The invention provides an ultrasonic treatment apparatus which can prevent components from dropping off even if a part of the assembly is broken.

The invention also provides an ultrasonic treatment system which can prevent incorrect combination of assemblies in the case where the assemblies are constructed.

What is claimed is:

1. An ultrasonic treatment apparatus comprising:
a vibrator assembly which generates ultrasonic vibration;
a probe which includes a proximal end detachably mounted to the vibrator assembly and a distal end having a treatment portion, the probe being configured to transmit the ultrasonic vibration from the proximal end to the treatment portion thereof;
a handle assembly to which the vibrator assembly and the probe are detachably mounted respectively, the handle assembly including a handle to be operated by an operator;
a treatment assembly which includes:
an action portion which faces the treatment portion of the probe and turns around with respect to the treatment portion;
a pipe-shaped drive member having a distal end and a proximal end, and is connected to the action portion at the distal end thereof and configured to transmit an operation force of the handle assembly from the proximal end to the distal end thereof, wherein the probe is slidably received within the pipe-shaped drive member;
a treatment assembly connecting member which is provided in the proximal end of the drive member, the treatment assembly connecting member being detachably mounted to the handle assembly; and
an outward projection portion formed in the distal end of the drive member, and protruding toward a radially outward direction, the treatment assembly being detachably mounted to the handle assembly when the action portion and the drive member are assembled; and
a sheath assembly covering an outer periphery of the treatment assembly, the sheath assembly including a sheath assembly connecting member which is detachably mounted to the handle assembly, and the sheath assembly being engaged with the outward projection portion of the treatment assembly at the distal end side of the drive member without disassembling parts,
wherein
the handle assembly includes a sheath connecting member connected to the sheath assembly connecting member and a drive member connecting member connected to the treatment assembly connecting member,
the sheath assembly connecting member includes at least two fixed arms extending to a proximal end side of the sheath, and
the fixed arms respectively include an outward protrusion portion that protrudes toward a radially outward direction and the outward protrusion portion being detachably engaged with the sheath connecting member.

2. The ultrasonic treatment apparatus according to claim 1 wherein
the sheath assembly includes a proximal end and a distal end,
the handle assembly includes a first mounting mechanism to which the proximal end of the drive member and the proximal end of the sheath assembly are detachably mounted, and
the treatment assembly includes a second mounting mechanism which is detachably attached to the first mounting mechanism.

3. The ultrasonic treatment apparatus according to claim 2 wherein the drive member includes the second mounting mechanism at the proximal end, the second mounting mechanism being detachably mounted to the first mounting mechanism.

4. The ultrasonic treatment apparatus according to claim 2, wherein the handle assembly includes an unlocking mechanism which releases a mounted state of the second mounting mechanism and the outward protrusion portion to separate the treatment assembly and the sheath assembly from the handle assembly.

5. The ultrasonic treatment apparatus according to claim 1 wherein
the drive member includes a drive pipe having a distal end and a proximal end and being configured to insert the probe thereinto,
the treatment assembly connecting member is provided in the proximal end of the drive pipe, and detachably mounted to the handle assembly,
an action portion support member is engaged by the distal end of the drive pipe, and is able to be relatively moved along an axial direction of the drive pipe, and
the action portion is pivoted so as to be able to be rotated with respect to the distal end of the action portion support member by proceeding and retreating of the drive pipe with respect to the action portion support member.

6. The ultrasonic treatment apparatus according to claim 5 wherein
the sheath assembly includes:
a long pipe having a distal end and a proximal end, an outer periphery of the drive pipe being covered with the long pipe, the long pipe being engaged with the action portion support member at the distal end; and
the sheath assembly connecting member is provided in the proximal end of the long pipe, and is connected to the distal end of the handle assembly.

7. The ultrasonic treatment apparatus according to claim 1 further comprising a drop-off preventing mechanism which prevents at least a part of a component of the treatment assembly from dropping off the treatment assembly when a large force is applied to the treatment assembly.

8. The ultrasonic treatment apparatus according to claim 7 wherein the drop-off preventing mechanism includes a sheath assembly which is detachably mounted to the distal end of the handle assembly.

9. The ultrasonic treatment apparatus according to claim 8 wherein
the treatment assembly includes a support member which is arranged in an outer periphery of the drive member while the support member is able to connect the action portion and the drive member, at least a part of the support member being formed in a cylindrical shape, and
the drop-off preventing mechanism includes:
an inward projection portion which is formed in the support member, the inward projection portion protruding toward a radially inward direction;
an outward projection portion which is formed in the support member, the outward projection portion protruding toward a radially outward direction;

a first recess which is formed in the drive member, the inward projection portion being engaged with the first recess; and a second recess which is formed in an inner peripheral surface of the sheath assembly, the outward projection portion being engaged with the second recess.

10. The ultrasonic treatment apparatus according to claim 9, wherein the first recess includes a hole in which the inward projection portion is engaged.

11. The ultrasonic treatment apparatus according to claim 10, wherein the second recess includes a cam groove in which the outward projection portion is engaged.

12. The ultrasonic treatment apparatus according to claim 10, wherein the treatment assembly includes a cylindrical member having an insulating property, the cylindrical member having a pipe shape configured to enable the insertion of the probe thereinto, the cylindrical member being brought into close contact with an inner surface of the distal end of the drive member, and the drop-off preventing mechanism includes an inward protrusion portion and a groove portion, at least a part of the drive member protrudes toward a radially inward direction, the inward protrusion portion being engaged in the groove portion, the groove portion being formed in at least a part of an outer peripheral surface of the cylindrical member.

* * * * *